(12) United States Patent
Ansorge et al.

(10) Patent No.: US 7,803,776 B2
(45) Date of Patent: Sep. 28, 2010

(54) COMBINED USE OF ENZYME INHIBITORS AND OF PHARMACEUTICAL COMPOSITIONS THEREOF

(75) Inventors: Siegfried Ansorge, Hohenwarte (DE); Uwe Lendeckel, Magdeburg (DE); Klaus Neubert, Halle (DE); Dirk Reinhold, Magdeburg (DE); Robert Vetter, Magdeburg (DE); Harald Gollnick, Magdeburg (DE)

(73) Assignee: Institut fur Medizintechnologie Magdeburg (IMTM) GmbH, Magdeburg (DE)

( * ) Notice: Subject to any disclaimer, the term of this patent is extended or adjusted under 35 U.S.C. 154(b) by 196 days.

(21) Appl. No.: 11/811,565

(22) Filed: Jun. 11, 2007

(65) Prior Publication Data
US 2007/0249541 A1 Oct. 25, 2007

Related U.S. Application Data

(62) Division of application No. 10/250,476, filed as application No. PCT/EP01/15199 on Dec. 21, 2001, now Pat. No. 7,229,969.

(30) Foreign Application Priority Data

| Jan. 2, 2001 | (DE) | 101 00 052 |
| Jan. 19, 2001 | (DE) | 101 02 392 |
| Nov. 9, 2001 | (DE) | 101 55 093 |

(51) Int. Cl.
  A61K 31/40 (2006.01)
  A61K 31/662 (2006.01)
  A61K 38/05 (2006.01)
  A61K 38/07 (2006.01)

(52) U.S. Cl. .............. 514/18; 514/14; 514/15; 514/16; 514/17; 514/19; 514/114; 514/119; 514/317; 514/326; 514/330; 514/365; 514/400; 514/422; 514/423; 514/576; 514/578; 514/579; 514/665

(58) Field of Classification Search ............... None
See application file for complete search history.

(56) References Cited

U.S. PATENT DOCUMENTS 6,096,713 A   8/2000   Green et al.

(Continued)

FOREIGN PATENT DOCUMENTS

DE   198 26 972 A1   12/1999

(Continued)

OTHER PUBLICATIONS

Riemann, et al.; Stimulation of the Expression and the Enzyme Activity of Aminopeptidase N/CD13 and Dipeptidylpeptidase IV/CD26 on Human Renal Cell Carcinoma Cells and Renal Tubular Epithelial Cells by T Cell-derived Cytokines, such as IL-4 and IL-13; DDFU-Abstract 1995-25180; Clin. Exp. Immunol., 1995, vol. 100, No. 2; 1 page.

(Continued)

Primary Examiner—Jeffrey E Russel
(74) Attorney, Agent, or Firm—Hodgson Russ LLP

(57) ABSTRACT

Provided are combinations of inhibitors of dipeptidyl peptidase IV (DP IV) and of enzymes having the same substrate specificity (DP IV-analogous enzymatic activity) and inhibitors of alanyl aminopeptidase (aminopeptidase N, APN) and of enzymes having the same substrate specificity (APN-analogous enzymatic activity) and use of the same to obtain a more than additive to superadditive inhibition for the treatment of arteriosclerosis, for the treatment of allergic reactions of the type I according to the Gell and Coombs classification and for the treatment of dermatological diseases with follicular and epidermal hyperkeratoses and an enhanced proliferation of keratinocytes.

19 Claims, 14 Drawing Sheets

U.S. PATENT DOCUMENTS

| | | | |
|---|---|---|---|
| 7,229,969 B2 * | 6/2007 | Ansorge et al. | 514/18 |
| 2005/0014699 A1 | 1/2005 | Ansorge et al. | |

FOREIGN PATENT DOCUMENTS

| | | |
|---|---|---|
| JP | 10218789 | 8/1998 |
| WO | WO 98/07421 | 2/1998 |
| WO | WO 98/44923 | 10/1998 |
| WO | WO 99/46272 | 9/1999 |
| WO | WO 01/89569 A1 | 11/2001 |

OTHER PUBLICATIONS

Schön, et al.; The Role of Dipeptidyl Peptidase IV in Human T Lymphocyte Activation. Inhibitors and Antibodies Against Dipeptidyl Peptidase IV Suppress Lymphocyte Proliferation and Immunoglobulin Synthesis in Vitro; Eur. J. Immunol., 1987, vol. 17; pp. 1821-1826.

CAPLUS-Abstract 1998:542897; JP 10218789; Ubenimex as Adjuvant for AIDS Vaccine; 1 page.

Corry et al.; Induction and Regulation of the IgE Response; Nature, Nov. 25, 1999, vol. 402; pp. B18-B23.

Barnes; Therapeutic Strategies for Allergic Diseases; Nature, Nov. 25, 1999, vol. 402; pp. B31-B38.

Vetter, et al.; BIOSIS-Abstract 1998:292458; DNA Synthesis in Cultured Human Keratinocytes and HaCaT Keratinocytes is Reduced by Specific Inhibition of Dipeptidylpeptidase IV (CD26) Activity; Journal of Dermatological Science, 1998, vol. 16, No. Suppl., 1; 1 page.

Hashimoto; WO 9807421 as WPIDS-Abstract 1998-168882 [15]; Inhibitors of Amino-Peptidase N-Enzyme and Neovascularisation Containing Aryl- or Cycloalkyl-Isoquinolinone, or New or Known Isoindolinone Compounds, or Their Thione Analogues; 1 page.

Thestrup-Pedersen, et al.; Medline -Abstract 84124029; Bestatin Therapy of Patients with Atopic Dermatitis; Acta-Dermato-Venereologica, 1983, vol. 63, No. 6; 1 page.

Ansorge, et al.; Membrane-Bound Peptidases of Lymphocytes: Functional Implications; Biomed. Biochim. Acta, 1991, vol. 50, No. 4-6; pp. 799-807.

Augustijns, et al.; Transport and Metabolism of Delta Sleep-Inducing Peptide in Cultured Human Intestinal Epithelial Cell Monolayers; Drug Metabolism and Disposition, 1995, vol. 23, No. 12; pp. 1372-1378.

Augustyns, et al.; The Unique Properties of Dipeptidyl-Peptidase IV (DPP IV/CD26) and the Therapeutic Potential of DPP IV Inhibitors; Current Medicinal Chemistry, 1999, vol. 6; pp. 311-327.

Hoffmann, et al.; Dipeptidyl Peptidase IV (CD 26) and Aminopeptidase N (CD 13) Catalyzed Hydrolysis of Cytokines and Peptides With N-Terminal Cytokine Sequences; FEBS 13371, December 1993, vol. 336, No. 1; Elsevier Science Publishers B.V.; pp. 61-64.

Kähne, et al.; Dipeptidyl Peptidase IV: A Cell Surface Peptidase Involved in Regulating T Cell Growth (Review); International Journal of Molecular Medicine, 1999, vol. 4; pp. 3-15.

Lendeckel, et al.; Role of Alanyl Aminopeptidase in Growth and Function of Human T Cells (Review); International Journal of Molecular Medicine, 1999, vol. 4; pp. 17-27.

Li, et al.; Abstract, Aminoacylpyrrolidine-2-Nitriles: Potent and Stable Inhibitors of Dipeptidyl-Peptidase IV (CD 26); Arch. Biochem. Biophys., 1995, vol. 323, No. 1; 1 page.

Reinhold, et al.; Inhibitors of Dipeptidyl Peptidase IV Induce Secretion of Transforming Growth Factor-$\beta_1$ in PWM-Stimulated PBMC and T Cells; Immunology, 1997, vol. 91; pp. 354-360.

Shimazawa, et al.; Novel Small Molecule Nonpeptide Aminopeptidase N Inhibitors With a Cyclic Imide Skeleton; J. Enzyme Inhibition, 1999, vol. 14; pp. 259-275.

Steinmetzer, et al.; Peptidyl Ammonium Methyl Ketones As Substrate Analog Inhibitors of Proline-Specific Peptidases; J. Enzyme Inhibition, 1993, vol. 7; pp. 77-85.

Stoeckel-Maschek, et al.; Abstract, Thioxo Amino Acid Pyrrolidides and Thiazolidides: New Inhibitors of Proline Specific Peptidases; Biochimica et Biophysica Acta, Jun. 15, 2000, vol. 1479, No. 1-2; 1 page.

Thielitz, et al.; Inhibitors of Dipeptidyl Peptidase IV and Aminopeptidase N Target Major Pathogenetic Steps in Acne Initiation; The Society for Investigative Dermatology, 2006; pp. 1-10.

Burge; Management of Darier's Disease; Clinical and Experimental Dermatology, 1999, vol. 24; pp. 53-56.

Wolfrum, et al.; Apstatin, a Selective Inhibitor of Aminopeptidase P, Reduces Myocardial Infarct Size by a Kinin-Dependent Pathway; Abstract—Br J Pharmacol, Sep. 2001, vol. 134(2); 1 page.

Prechel, et al.; Effect of a New Aminopeptidase P Inhibitor, Apstatin, on Bradykinin Degradation in the Rat Lung; Abstract—J Pharmacol Exp Ther., Dec. 1995, vol. 275(3); 1 page.

Ansorge, et al.; Cancerlit 92198405; Membrane-Bound Peptidases of lymphocytes: Functional Implications; Biomedica Biochimica Acta, 1991, vol. 50, No. 4-6; 1 page.

Biewenga, et al.; The Pharmacology of the Antioxidant Lipoic Acid; Gen. Pharmac., 1997, vol. 29, No. 3; pp. 315-331.

* cited by examiner

COMBINED USE OF ENZYME INHIBITORS AND OF PHARMACEUTICAL COMPOSITIONS THEREOF

This application is a divisional application of U.S. application Ser. No. 10/250,476, filed Feb. 12, 2004, which is a national phase application of International Application serial no. PCT/EP01/15199, filed Dec. 21, 2001, which claims priority to German Application Serial No. DE 10100052.9, filed Jan. 2, 2001, and to German Application Serial No. DE 10102392.8, filed Jan. 19, 2001, and to German Application Serial No. DE 10155093.6, filed Nov. 9, 2001; the entire disclosures of each of the aforementioned applications are incorporated herein by reference.

BACKGROUND OF THE INVENTION

It has been shown that membrane-located peptidases as, for example, DP IV or APN play a key role in the process of the activation and clonal expression of immune cells, particularly of T lymphocytes [Fleischer B: CD26 a surface protease involved in T cell activation. Immunology Today 1994; 15:180-184; Lendeckel U et al.: Role of alanyl aminopeptidase in growth and function of human T cells. International Journal of Molecular Medicine 1999; 4:17-27; Riemann D et al.: CD13—not just a marker in leukemia typing. Immunology Today 1999; 20:83-88]. Several functions of mitogen-stimulated mononuclear cells (MNC) or α-cumulated T lymphocytes as, for example, DNA synthesis production and secretion of immune-stimulating cytokines (IL-2, IL-6, IL-12, IFN-γ) and helper functions of B cells (synthesis of IgG and IgM) may be inhibited in the presence of specific inhibitors of DP IV and APN [Schön E et al.: The dipeptidyl peptidase IV, a membrane enzyme involved in the proliferation of T lymphocytes. Biomed. Biochim. Acta 1985; 2: K9-K15; Schön E et al.: The role of dipeptidyl peptidase IV in human T lymphocyte activation. Inhibitors and antibodies against dipeptidyl peptidase IV suppress lymphocyte proliferation and immunoglobulin synthesis in vitro. Eur. J. Immunol. 1987; 17: 1821-1826; Reinhold D et al.: Inhibitors of dipeptidyl peptidase IV induce secretion of transforming growth factor β1 in PWM-stimulated PBMNC and T cells. Immunology 1997; 91: 354-360; Lendeckel U et al.: Induction of the membrane alanyl aminopeptidase gene and surface expression in human T cells by mitogenic activation. Biochem. J. 1996; 319: 817-823; Kähne T et al.: Dipeptidyl peptidase IV: A cell surface peptidase involved in regulating T cell growth (Review). Int. J. Mol. Med. 1999; 4: 3-15; Lendeckel U et al.: Role of alanyl aminopeptidase in growth and function of human T cells (Review). Int. J. Mol. Med. 1999; 4: 17-27].

On the other hand, scientific discoveries of the recent years characterized arteriosclerosis as an inflammatory disease, whereby T lymphoctes play a decisive role in the development and progress of said disease [Ross R: Arteriosclerosis—an inflammatory disease. New England J. Med. 1999; 340 (2): 115-126]. According to those discoveries, arteriosclerotic lesions are understood as a series of specific cellular and molecular reactions which, when taken together, are to be characterized as inflammations, unequivocally. Such lesions primarily occurring in large and medium size elastic and muscular arteries result into ischemia (disturbed circulation) of the heart, of the cerebrum and of the extremities up to infarcts of the above-mentioned organs. Arteriosclerotic lesions are formed at defined arterial locations, where branches and curves effect characteristic changes of the blood flow and of the sheer stresses as well as the creation of turbulences [Gotlieb A I et al.: The role of rheology in atherosclerotic coronary artery disease. In: Fuster V, Ross R, Topol E J, eds. Atherosclerosis and coronary athery disease. Vol. 1 Philadelphia: Lippincott-Raven, 1996: 595-606]. Vessel endothel cells generate specific molecules at those locations, which molecules are responsible for the attraction, binding, accumulation and activation of T lymphocytes and monocytes. T lymphocytes are essential inflammatory cells in all phases of the arteriogenesis. T cells infiltrate from the peripheral blood into the arteriosclerotic plaques and multiply at the lesion location [Jonasson L et al.: Regional accumulation of T cells, macrophages and smooth muscle cells in the human atherosclerotic plaque. Arteriosclerosis. 1986; 6: 131-138; van der Wal A C et al.: Atherosclerotic lesions in humans: in situ immunophenotypic analysis suggesting an immune mediated response. Lab. Invest. 1989; 61: 166-[70]. As a result of the accumulation, at the location of an arteriosclerotic lesion, of such activated T lymphocytes which are characterized by a strong expression of alanyl aminopeptidase and of dipeptidyl peptidase IV, chemokines, cytokines, growth factors and proteases are released, which compounds effect a further intensification of the disease conditions, as other immune cells are recruited and activated [Libby P and Ross R. Cytokines and growth regulatory molecules. In: Fuster V, Ross R, Topol E J, eds. Atherosclerosis and coronary athery disease. Vol. 1, Philadelphia: Lippincott-Raven, 1996: 585-594].

In addition, monocytes localized in arteriosclerotic plaques are characterized by the constitutive expression of, for example, alanyl aminopeptidase (APN). The same is true for endothelic cells which express those ectopeptidases, too.

The angiotensin-converting enzyme plays a particular role in the pathogenesis of arteriosclerosis. Said enzyme effects the generation of angiotensin II (ang II) from ang I, the former substance severely increasing the blood pressure. Hypertension is an important factor promoting the risk of arteriosclerosis, and patients suffering therefrom often have increased ang II blood levels. In addition, ang II is pro-arterogeneous by stimulating the growth of the smooth muscles (vessels) [Chobanian A V et al. Renin angiotensin system and atherosclerotic vascular disease. In: Fuster V, Ross R, Topol E J, eds. Atherosclerosis and coronary athery disease. Vol. 1, Philadelphia: Lippincott-Raven, 1996: 237-242; Gibbons G H et al. Vascular smooth muscle cell hypertrophy vs. hyperplasia: autocrine TGF-β1 expression determines growth response to angiotensin II. J. Clin. Invest. 1992; 90: 456-461]. Moreover, ang II also enhances the inflammatory reaction by an increase of the lipoxygenase activity whereby inflammationpromoting mediators are released in increasing amounts.

SUMMARY OF THE INVENTION

The present invention relates to the inhibition of the DNA synthesis and, thus, the proliferation of immune cells by the combined effect of inhibitors of aminopeptidase N (APN; E.C. 3.4.11.2; CD13), of dipeptidyl peptidase IV (DP IV; E.C. 3.4.14.5; CD26), of prolyl oligopeptidase (POP; prolyl endopeptidase; PEP; E.C. 3.4.21.26), of the membrane-located aminopeptidase P (X-Pro-Aminopeptidase; APP; XPNPEP2; E.C. 3.4.11.9) and of the angiotensin-converting enzyme (Angiotensin-konvertierendes Enzym; ACE; E.C. 3.4.15.1, CD143) or by the combined inhibition, respectively, of the activity of the above-mentioned enzymes as a result of the simultaneous application of respective specific inhibitors of said enzymes on the basis of amino acid derivatives, peptides or peptide derivatives, by which the activation, the DNA synthesis and, thus, the proliferation of immune cells is suppressed.

The invention also relates to the inhibition of the DNA synthesis essential for the proliferation as well as to the inhibition of the production of cytokines (interleukin-4, IL-4) by TH2 cells by a combined effect of inhibitors of aminopeptidase N (APN; E.C. 3.4.11.2; CD13) and of dipeptidyl peptidase IV (DP IV; E.C. 3.4.14.5; CD26) as a result of a simultaneous application of respective specific inhibitors of said enzymes on the basis of amino acid derivatives, peptides or peptide derivatives, by which the activation, the proliferation (DNA synthesis) and cytokine production (IL-4) by TH2 cells is suppressed.

The invention also relates to the inhibition of the DNA synthesis of keratinocytes essential for the proliferation by a combined effect of inhibitors of aminopeptidyl peptidase N (APN; E.C. 3.4.11.2; CD13) and of dipeptidyl peptidase IV (DP IV; E.C. 3.4.14.5; CD26) as a result of the simultaneous or immediately sequential application of the respective specific inhibitors of said enzymes or of enzymes having a similar effect on the basis of amino acid derivatives, peptides or peptide derivatives, by which the proliferation (DNA synthesis) of keratinocytes is suppressed.

The present invention is applicable to all diseases with an autoimmune pathogenesis that the disease and its course of genesis and progress is based on, or consists of, an activation and proliferation of immune cells, particularly of autoreactive T cells. Similar mechanisms are effective for a number of inflammatory diseases as, for example arteriosclerosis, where T lymphocytes play a central role in the development and chronification of the disease.

DESCRIPTION OF THE INVENTION

Figure 1:
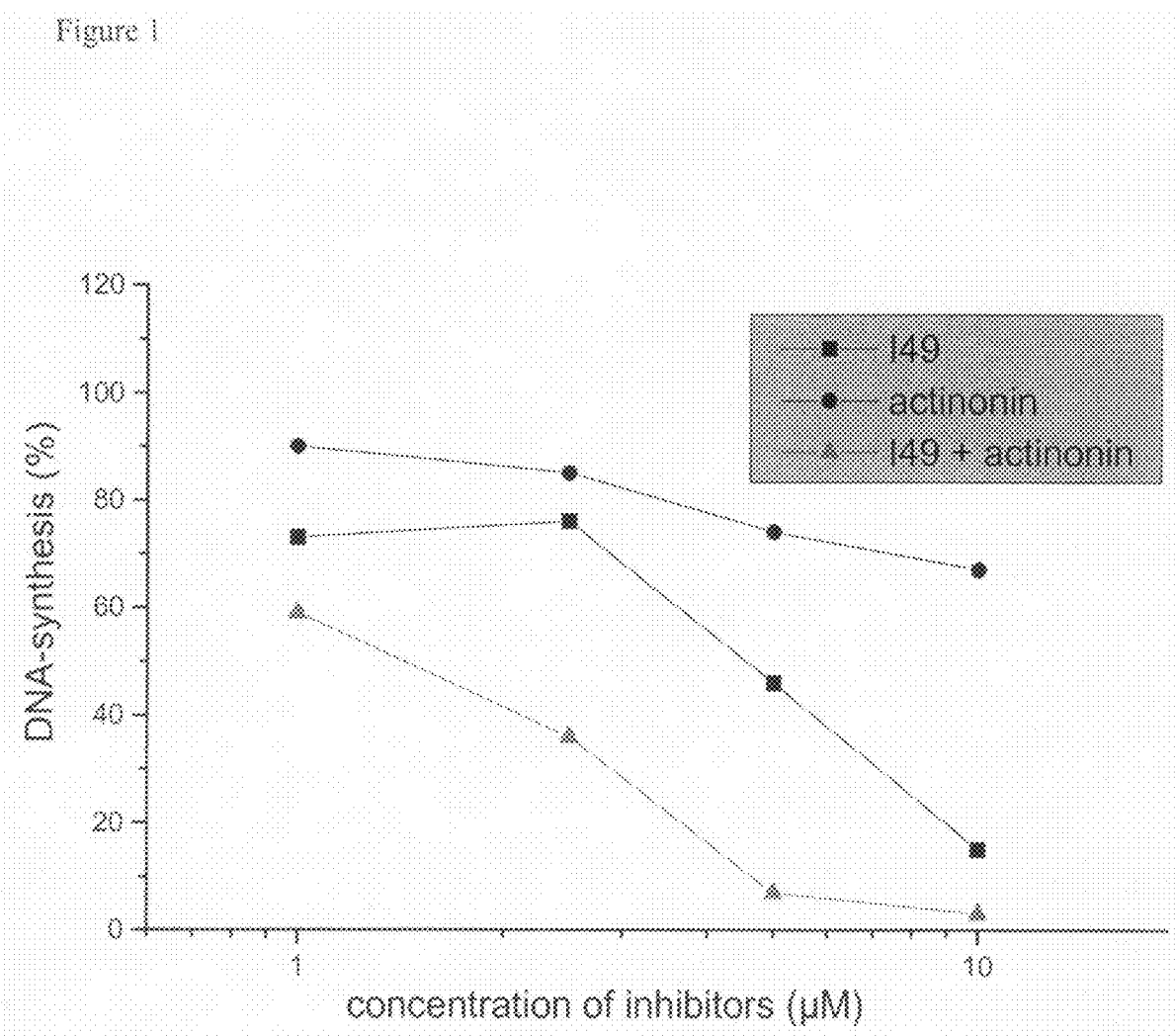
FIG. 1: Synergistic and dose-dependent effect of inhibitors of DP IV (149) and of aminopeptidase N (actinonin) on the DNA synthesis of human T lymphocytes. Human peripheral T cells were incubated for three days with the above-indicated concentrations of the inhibitors. Subsequently, $^3$-[H]-methyl thymidine was added to the culture medium, and after further 6 hours, the $^3$-[H]-thymidine amount incorporated into the DNA was measured.

The present invention is based on the surprising finding that the simultaneous effect of inhibitors of the enzyme activity, or the simultaneous influence of the biologic activity, of (I) dipeptidyl peptidase IV and amino peptidase N; (II) dipeptidyl peptidase IV and the "angiotensin-converting enzyme"; (III) dipeptidyl peptidase IV and prolyl oligopeptidase; as well as (IV) dipeptidyl peptidase IV and X-Pro amino peptidase inhibits the DNA synthesis and, thus, the proliferation of mononuclear cells (MNC) and of T cells to an extent which cannot be achieved by an application of a single one of those enzyme inhibitors, including the case of the administration of an enhanced dose thereof. Although said inhibitors finally influence the same process, namely the DNA synthesis and, thus, the proliferation of immune cells, this effect is substantially less pronounced and is not long-lasting. Due to the functional overlap of the enzymatic activity of the above-mentioned enzymes, there results a more than additive or super-additive inhibitory effect on the synthesis of DNA and the proliferation from the simultaneous inhibition of two or more of those enzymes, as the data of the present invention show.

The invention shows that the simultaneous application of inhibitory substances of the above-mentioned enzymes or the simultaneous application of corresponding preparations and administration forms, respectively, is definitely suitable for a therapy of inflammatory diseases as, for example, of arteriosclerosis, for the development of which the proliferation and activation of T lymphocytes plays a central and important role.

In detail, the invention is based on the finding that the DNA synthesis of mononuclear cells (MNC) and T cells is inhibited, in a more than additive to super-additive manner, by a simultaneous administration of substances inhibiting the enzymatic activity of (I) dipeptidyl peptidase IV and amino peptidase N;
(II) dipeptidyl peptidase IV and the "angiotensin-converting enzyme";
(III) dipeptidyl peptidase IV and prolyl oligopeptidase;
(IV) dipeptidyl peptidase IV and X-Pro amino peptidase.

The application of enzyme inhibitors is a novel method and a supplementary form of therapy for the above-mentioned diseases.

The inhibitors of dipeptidyl peptidase IV, of amino peptidase N, of prolyl oligopeptidase, of the "angiotensin-converting enzyme" and of X-Pro amino peptidase applied in accordance with the present invention may be applied in the form of pharmaceutically applicable formulation complexes as inhibitors, substrates, pseudo-substrates, peptides having inhibitory effect and peptide derivatives as well as antibodies for this enzyme. Preferred effectors for DP IV are, for example, Xaa-Pro dipeptides corresponding derivatives, preferably dipeptide phosphonic acid diaryl esters, dipeptide boronic acids (e.g. Pro-boro-Pro) and their salts, Xaa-Xaa-(Trp)-Pro-(Xaa)$_n$ peptides (n=0 to 10), corresponding derivatives and their salts, or amino acid-(Xaa) amides, corresponding derivatives and their salts, wherein Xaa is an α-amino acid or -imino acid or an α-amino acid derivative or -imino acid derivative, respectively, preferably N$^ε$-4-nitrobenzyloxycarb-onyl-L-lysine, L-proline, L-tryptophane, L-isoleucine, L-valine, and cyclic amines as, for example pyrrolidine, piperidine, thiazolidine, and their derivatives serve as the amide structure. Such compounds and their preparation were described in an earlier patent (K. Neubert at al., DD 296 075 A5).

The inhibitors are administered simultaneously with known carrier substances. The administration may occur, on the one hand, in the form of a topical application by means of cremes, ointments, pastes, gels, solutions, sprays, liposomes, shaken mixtures, hydrocolloid dressings and other dermatologic bases/vehicles including instillative application and, on the other hand, in the form of a systemic application for an oral, transdermal, intravenous, subcutaneous, intracutaneous or intramuscular application in suitable formulations or in a suitable galenic form.

It was found for allergic reactions of the type I as, for example asthma bronchiale or hay fever that the diseases are based on an activation, proliferation, and the production of cytokines (in particular IL-4) by immune cells, particularly by TH2 cells [D. D. Corry et al., Induction and regulation of the IgG response. Nature 1999; 402: B18 to B23].

It was shown that membrane-located peptidases as, for example, DP IV or APN play a key role in the process of the activation and clonal expression of immune cells, particularly of T lymphocytes [Fleischer B: CD26 a surface protease involved in T cell activation. Immunology Today 1994; 15:180-184; Lendeckel U et al.: Role of alanyl amino-peptidase in growth and function of human T cells. International Journal of Molecular Medicine 1999; 4:17-27; Riemann D et al.: CD13—not just a marker in leukemia typing. Immunology Today 1999; 20:83-88]. Several functions of mitogen-stimulated mononuclear cells (MNC) or accumulated T lymphocytes as, for example, DNA synthesis production and secretion of immune-stimulating cytokines (IL-2, IL-6, IL-12, IFN-γ) and helper functions of B cells (synthesis of IgG and IgM) may be inhibited in the presence of specific inhibitors of DP IV and APN [Schön E et al.: The dipeptidyl peptidase IV, a membrane enzyme involved in the proliferation of T lymphocytes. Biomed. Biochim. Acta 1985; 2: K9-K15; Schön E et al.: The role of dipeptidyl peptidase IV in human T lymphocyte activation. Inhibitors and antibodies against dipeptidyl peptidase IV suppress lymphocyte proliferation and immunoglobulin synthesis in vitro. Eur. J. Immunol. 1987; 17: 1821-1826; Reinhold D et al.: Inhibitors of dipeptidyl peptidase IV induce secretion of transforming growth factor β1 in PWM-stimulated PBMNC and T cells. Immunology 1997; 91: 354-360; Lendeckel U et al.: Induction of the membrane alanyl aminopeptidase gene and surface expression in human T cells by mitogenic activation. Biochem. J. 1996; 319: 817-823; Kähne T et al.: Dipeptidyl peptidase IV: A cell surface peptidase involved in regulating T cell growth (Review). Int. J. Mol. Med. 1999; 4: 3-15; Lendeckel U et al.: Role of alanyl aminopeptidase in growth and function of human T cells (Review). Int. J. Mol. Med. 1999; 4:17-27].

On the other hand, scientific discoveries of the recent years characterized an allergic reaction of the type I as an inflammatory disease, whereby TH12 lymphocytes play a decisive role in the development and chronification of said disease [D. D. Corry et al.: Induction and regulation of the IgE response. Nature 1999; 402: B18-B23. P. J. Barnes: Therapeutic strategies for allergic diseases. Nature 1999; 402: B31-B38].

IL4 is a helper cytokine for the B cell proliferation, stimulates the generation of IgE and the expression of Fc-IgE receptors of low affinity. Moreover, IL-4 enhances the induction of TH2 cells themselves and controls the proliferation and activity of eosinophilic cells and mast cells. That is why it plays a central role in allergic reactions of the type I [D. P. Stites, A. I. Terr, T. G. Parslow: Medical Immunology. Appelton & Lange, Stamfort, Conn., 1997].

The present invention is also based on the surprising finding that the simultaneous effect of inhibitors of dipeptidyl peptidase IV and amino peptidase N inhibits the proliferation (DNA synthesis) of and the production of LI-4 by mitogen-stimulated mononuclear cells (MNC) to an extent which cannot be achieved by an application of a single one of those enzyme inhibitors, including the case of an enhanced dose thereof. Although said inhibitors finally influence the same process, namely the DNA synthesis and, thus, the proliferation of and the IL-4 production by TH2 cells, this effect is substantially less pronounced, when the inhibitors are applied singly, and is not long-lasting. Due to the functional overlap of the enzymatic activity of the above-mentioned enzymes, there results a more than additive or super-additive inhibitory effect on the synthesis of DNA and the proliferation from the simultaneous inhibition of the two enzymes, as the data of the present invention show.

The invention shows that the simultaneous application of inhibitory substances of the enzymes DP IV and APN or the simultaneous application of corresponding preparations and administration forms, respectively, is definitely suitable for a therapy of allergic diseases of the type I, for the development of which the proliferation and activation of T lymphocytes plays a central and important role.

In detail, the invention is based on the finding that the DNA synthesis of, and the IL-4 production by, mononuclear cells (MNC) is inhibited, in a more than additive to super-additive manner, by a simultaneous administration of substances inhibiting dipeptidyl peptidase IV and amino peptidase N.

The application of enzyme inhibitors is a novel method and a supplementary form of therapy for the above-mentioned diseases.

The inhibitors of dipeptidyl peptidase IV and of amino peptidase N applied in accordance with the present invention may be applied in the form of pharmaceutically applicable formulation complexes as inhibitors, substrates, pseudo-substrates, peptides having inhibitory effect and peptide derivatives as well as antibodies for this enzyme. Preferred effectors for DP IV are, for example, Xaa-Pro dipeptides corresponding derivatives, preferably dipeptide phosphonic acid diaryl esters, dipeptide boronic acids (e.g. Pro-boro-Pro) and their salts, XaaXaa-(Trp)-Pro-(Xaa)$_n$ peptides (n=0 to 10), corresponding derivatives and their salts, or amino acid-(Xaa) amides, corresponding derivatives and their salts, wherein Xaa is an α-amino acid or -imino acid or an α-amino acid derivative or -imino acid derivative, respectively, preferably N$^\epsilon$-4-nitrobenzyloxycarb-onyl-L-lysine, L-proline, L-tryptophane, L-isoleucine, L-valine, and cyclic amines as, for example pyrrolidine, piperidine, thiazolidine, and their derivatives serve as the amide structure. Such compounds and their preparation were described in an earlier patent (K. Neubert at al., DD 296 075 A5).

Preferred inhibitors of alanyl aminopeptidase are bestatin (Ubenimex), actinonin, probestine, phebestine, RB3014 or leuhistine.

The inhibitors are administered simultaneously with known carrier substances. The administration may occur, on the one hand, in the form of a topical application by means of cremes, ointments, pastes, gels, solutions, sprays, liposomes, shaken mixtures, hydrocolloid dressings and other dermatologic bases/vehicles including instillative application and, on the other hand, in the form of a systemic application for an oral, transdermal, intravenous, subcutaneous, intracutaneous or intramuscular application in suitable formulations or in a suitable galenic form.

A number of dermatologic diseases are accompanied by follicular and epidermal hyperkeratoses and an increased proliferation of keratinocytes. Such diseases cover inflammatory and non-inflammatory epidermal hyperproliferation conditions (e.g. congenital ichthyoses and psoriasis), benign and malign epidermal clonal expansions (e.g. warts, condylomes, actinic keratoses/precanceroses), benign and malign follicular hyperproliferation conditions (e.g. keratosis follicularis) as well as benign and malign epithelial adnex tumors and primary and reactive nail cell hyperproliferations. Details are set out in Table 1.

Peptidases as, for example, dipeptidyl peptidase IV and amino peptidase N or similarly acting enzymes are of particular importance for the regulation and modulation, respectively, of interactions between cells, since they are, inter alia, located, as ectoenzymes, in the plasma membrane of the cells, interact with other extracellular structures, activate or inactivate peptidergic messenger substances by an enzyme-catalysed hydrolysis and, thus, are important for the intercellular communication [Yaron A, et al.: Proline-dependent structural and biological properties of peptides and proteins. Crit Rev Biochem Mol Biol 1993; 28:31-81; Vanhoof G, et al.: Proline motifs in peptides and their biological processing. FASEB J 1995; 9:736-744].

It was shown that membrane-located peptidases as, for example, DP IV or APN play a key role in the process of the activation and clonal expression of immune cells, particularly of T lymphocytes [Fleischer B: CD26 a surface protease involved in T cell activation. Immunology Today 1994; 15:180-184; Lendeckel U et al.: Role of alanyl amino-peptidase in growth and function of human T cells. International Journal of Molecular Medicine 1999; 4:17-27; Riemann D et al.: CD13—not just a marker in leukemia typing. Immunology Today 1999; 20:83-88]. Several functions of mitogen-stimulated mononuclear cells (MNC) or accumulated T lymphocytes as, for example, DNA synthesis production and secretion of immune-stimulating cytokines (IL-2, IL-6, IL-12, IFN-γ) and helper functions of B cells (synthesis of IgG and IgM) may be inhibited in the presence of specific inhibitors of DP IV and APN [Schön E et al.: The dipeptidyl peptidase IV, a membrane enzyme involved in the proliferation of T lymphocytes. Biomed. Biochim. Acta 1985; 2: K9-K15; Schön E et al.: The role of dipeptidyl peptidase IV in human T lymphocyte activation. Inhibitors and antibodies against dipeptidyl peptidase IV suppress lymphocyte proliferation and immunoglobulin synthesis in vitro. Eur. J. Immunol. 1987; 17: 1821-1826; Reinhold D et al.: Inhibitors of dipeptidyl peptidase IV induce secretion of transforming growth factor β1 in PWM-stimulated PBMNC and T cells. Immunology 1997; 91: 354-360; Lendeckel U et al.: Induction of the membrane alanyl aminopeptidase gene and surface expression in human T cells by mitogenic activation. Biochem. J. 1996; 319: 817-823; Kähne T et al.: Dipeptidyl peptidase IV: A cell surface peptidase involved in regulating T cell growth (Review). Int. J. Mol. Med. 1999; 4: 3-15; Lendeckel U et al.: Role of alanyl aminopeptidase in growth and function of human T cells (Review). Int. J. Mol. Med. 1999; 4: 17-27]. It is already known that a treatment of autoimmune diseases and transplant rejection is possible by an inhibition of dipeptidyl peptidase IV located on immune cells by means of synthetic inhibitors. (e.g. EP 0 764 151 A1; WO 95/29691; EP 0 731 789 A1; EP 0 528 858 A1).

The present invention is also based on the surprising finding that the simultaneous effect of inhibitors of dipeptidyl peptidase IV/CD26 expressed in or on keratinocytes and of amino peptidase N/CD13 or similar enzymes inhibits the proliferation (DNA synthesis) of those cells to an extent which cannot be achieved by an application of a single one of those enzyme inhibitors, administered at a given dose. Although said inhibitors finally influence the same process, namely the DNA synthesis and, thus, the proliferation of the keratinocytes, this effect is substantially less pronounced, when the inhibitors are applied singly, and is not long-lasting. Due to the functional overlap of the enzymatic activity of the above-mentioned enzymes, there results an additive inhibitory effect and, at lower concentrations, a more than additive or super-additive inhibitory effect on the synthesis of DNA and the proliferation from the simultaneous inhibition of the two enzymes, as the data of the present invention show.

The invention shows that the simultaneous application of inhibitory substances of the enzymes DP IV and APN or of similar enzymes or the simultaneous application of corresponding preparations and administration forms, respectively, is definitely suitable for a therapy or prevention of inflammatory and non-inflammatory epidermal hyperproliferation conditions (e.g. congenital ichthyoses and psoriasis), benign and malign epidermal clonal expansions (e.g. warts, condylomes, actinic keratoses/precanceroses), benign and malign follicular hyperproliferation conditions (e.g. keratosis follicularis) as well as benign and malign epithelial adnex tumors and primary and reactive nail cell hyperproliferations, for the development of which the proliferation and activation of epidermal and follicular keratinocytes as well as of keratinocytes of the transitional mucous membrane zone is of central importance.

In addition to keratinocytes, T lymphocytes, too, play a central role in inflammatory diseases of the skin, in particular in autoimmune diseases like psoriasis. As keratinocytes, T cells express the above-mentioned peptidases DP IV and APN. As a consequence, the therapeutic effect claimed or protected, respectively, for keratinocytes is even enhanced by influencing T cells. This is also subject of the German Patent Application No. 100 25 464.0 entitled "Combined Use of Enzyme Inhibitors and of Pharmaceutical Preparations Thereof for a Therapy of Autoimmune Diseases as, for example, Rheumatoid Arthritis, Lupus Erythematodes, Multiple Sclerosis, Insuline-Dependent Diabetes Mellitus (IDDM), Crohn's Disease, Colitis Ulcerosa, Psoriasis, Neurodermitis, Glomerulonephritis, interstitial Nephritis, Vasculitis, Autoimmune Thyroid Gland Diseases or Autoimmune Hemolytic Anemia as well as transplantations and tumor diseases".

In detail, the invention is based on the finding that the DNA synthesis of HaCaT keratinocytes is inhibited, in an additive manner and, at lower concentrations in a super-additive manner, by a simultaneous administration of inhibitors of dipeptidyl peptidase IV and amino peptidase N.

Up to now, the above-mentioned diseases were treated topically by administering antiproliferative and differentiating substances (salicylic acid, urea, endogenous and synthetic retinoids, Vitamin D3 derivatives, corticosteroids) as well as systemically by administering partially immunosuppressive and antiproliferative preparations (e.g. Cyclosporin A, corticosteroids, retinoids). Particularly when administering substances systemically, often undesired side effects were observed. The combined administration of inhibitors of DP IV and APN is a novel, expectedly very effective, possibly cheap therapeutical method and a valuable alternative constituent element of the existing therapy concepts.

The inhibitors of dipeptidyl peptidase IV and of amino peptidase N or of similar enzymes applied in accordance with the present invention may be applied in the form of pharmaceutically applicable formulation complexes as inhibitors, substrates, pseudo-substrates, peptides having inhibitory effect and peptide derivatives as well as antibodies for this enzyme. Preferred effectors for DP IV are, for example, Xaa-Pro dipeptides corresponding derivatives, preferably dipeptide phosphonic acid diaryl esters, dipeptide boronic acids (e.g. Pro-boro-Pro) and their salts, Xaa-Xaa-(Trp)-Pro-(Xaa)$_n$ peptides (n=0 to 10), corresponding derivatives and their salts, or amino acid-(Xaa) amides, corresponding derivatives and their salts, wherein Xaa is an α-amino acid or -imino acid or an α-amino acid derivative or -imino acid derivative, respectively, preferably $N^\epsilon$-4-ni-trobenzyloxycarbonyl-L-lysine, L-isoleucine, L-valine, L-tryptophane, L-proline, and cyclic amines as, for example pyrrolidine, piperidine, thiazolidine, and their derivatives serve as the amide structure. Such compounds and their preparation were described in an earlier patent (K. Neubert at al., DD 296 075 A5).

Preferred inhibitors of alanyl aminopeptidase are bestatin (Ubenimex), actinonin, probestine, phebestine, RB3014 or leuhistine.

The inhibitors are administered simultaneously with known carrier substances. The administration may occur, on the one hand, in the form of a topical application by means of cremes, ointments, pastes, gels, solutions, sprays, liposomes, shaken mixtures, hydrocolloid dressings, plasters and similar new carries substrates, jet injections and other dermatologic bases/vehicles, respectively, including instillative application and, on the other hand, in the form of a systemic application for an oral, transdermal, intravenous, subcutaneous, intracutaneous or intramuscular application in suitable formulations or in a suitable galenic form.

TABLE 1

| e.g. non-inflammatory | e.g. inflammatory |
|---|---|
| Epidermal hyperproliferation conditions | |
| Congenital Ichthyoses | Psoriasis and sub-types including nails and hair |
| Acquired ichthyoses (paraneoplast.) | Lichen ruber and subtypes Parapsoriasis group |
| Palmoplantar keratoses congenital acquired/paraneoplast. | Keratosis lichenoides Lichen simplex chronicus + reactive lichenoid hyperproliferations (e.g. atopic dermatitis) |
| M. Darier | Lichenoid reactions at GvHD |
| Epidermal Naevi | ILVEN-Naevus |

TABLE 1-continued

| | |
|---|---|
| Cutis rhomboidalis nuchae | Lupus Erythematodes chron.disc./ SCLE/SLE |
| Acanthosis nigricans | Pityriasis rubra pilaris |
| Pachydermia | M. Grover |
| | Vitiligo |
| | Erythrodermia accompanied by a hyperproliferation of keratinocytes |
| benign | malign |
| Epidermal clonal expansion ||
| HPV associated (warts, condylomes) | HPV associated tumors |
| Seborrhoic keratoses | Actinic keratoses/precanceroses |
| Hidroacanthomes/poromes | M. Bowen + Bowen-CA |
| Epidermal cysts | M. Paget + Paget-CA |
| Milias | plate epithel-CA |
| M. Gottron | Merkel cell-CA |
| Follicular hyperproliferation conditions ||
| Keratosis follicularis | Hair follicular cell tumors |
| Follicular hyperkeratoses | Proliferating trichilemmal cysts |
| Ulerythema ophryogenes | Mixed tumors |
| Hypertrichoses | |
| Trichilemmal cysts | |
| Epithelial adnex tumors ||
| Poroms | eccrinic/apocrinic CA's + Subtypes |
| Syringoductal tumors | |
| Hidraadenomas | |
| Spiraadenomas | |
| Cylindromas | |
| Primary and reactive nail cell hyperproliferation ||
| Congenital (e.g. pachyonchias) | Non-infectious |
| | Acquired |
| | Infectious with mycoses |

The invention is further explained by means of the following working examples, but is not limited to these preferred embodiments.

EXAMPLE 1

Inhibition of the DNA Synthesis of Human T Lymphocytes by an Incubation with Synthetic Inhibitors of DP IV and of APN The searches according to the invention show that the DNA synthesis of human peripheral T lymphocytes is inhibited, in a more than additive to superadditive manner, by a simultaneous administration of inhibitors of DP IV (Lys[Z(NO$_2$)]-thiazolidide=I49) and of APN (Actinonin). The T cells were incubated for 72 h in the presence of said inhibitors, and the DNA synthesis was determined subsequently by a measurement of the $^3$-[H]-thymidine incorporation, as described by Reinhold et al. (Reinhold D. et al.: Inhibitors of dipeptidyl peptidase TV induce secretion of transforming growth factor 131 in PWM-stimulated PBMNC and T cells; Immunology 1997, 91: 354-360). FIG. 1 (page 1/14) shows the dose-dependent, more than additive to superadditive inhibition of the DNA synthesis.

EXAMPLE 2

Figure 2:
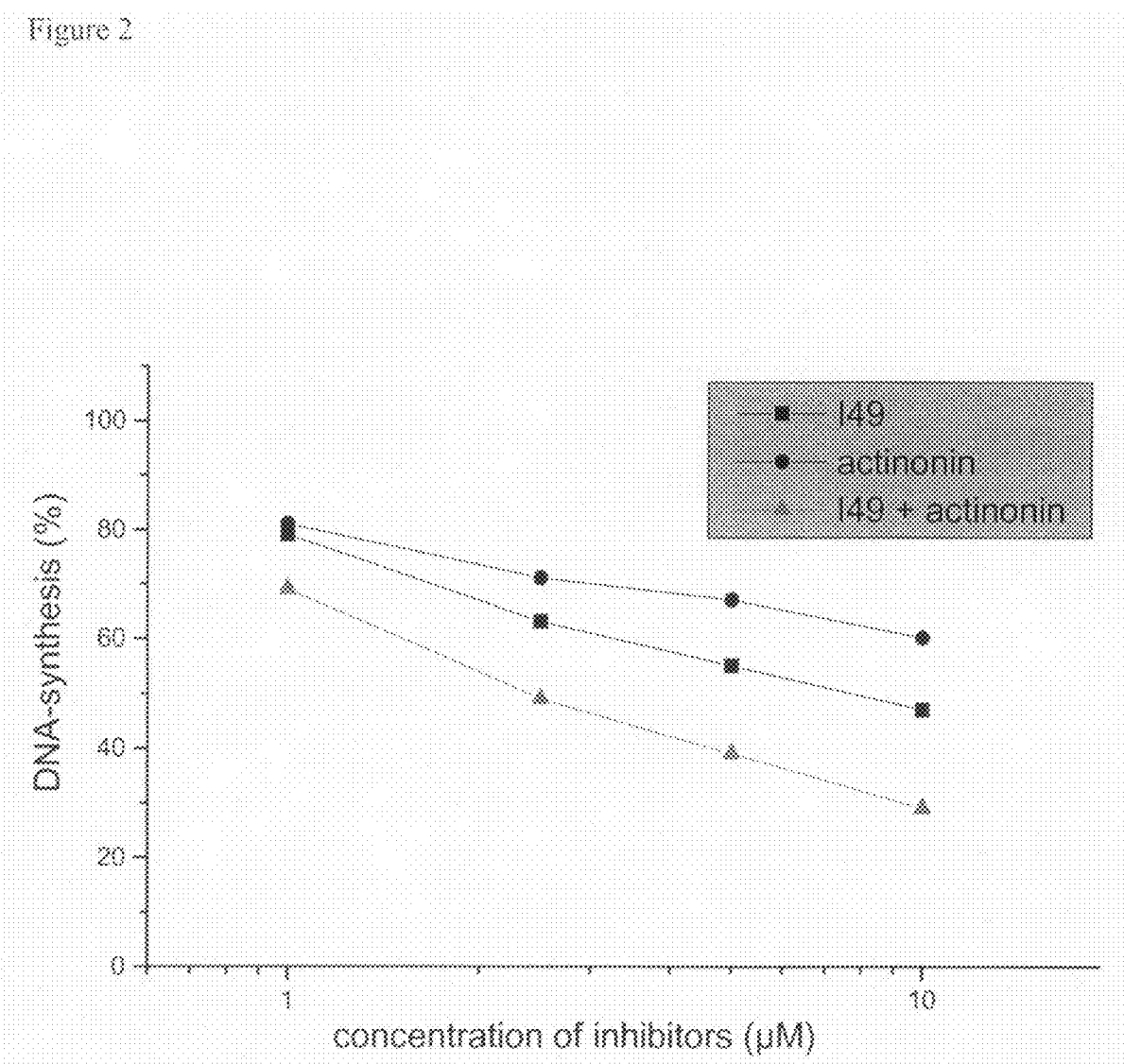
FIG. 2: Synergistic and dose-dependent effect of inhibitors of DP IV (149) and of APN (actinonin) on the DNA synthesis of human mononuclear cells (MNC). Human MNC were incubated for three days with the above-indicated concentrations of the inhibitors. Subsequently, $^3$-[H]-methyl thymidine was added to the culture medium, and after further 6 hours, the $^3$-[H]-thymidine amount incorporated into the DNA was measured.

Inhibition of the DNA Synthesis of Human Peripheral Mononuclear Cells by an Incubation with Synthetic Inhibitors of DP IV and of APN The searches according to the invention show that the DNA synthesis of human peripheral mononuclear cells (MNC) is inhibited, in a more than additive to superadditive manner, by a simultaneous administration of inhibitors of DP IV (Lys[Z(NO$_2$)]-thiazolidide=I49) and of APN (Actinonin). The MNC were incubated for 72 h in the presence of said inhibitors, and the DNA synthesis was determined subsequently by a measurement of the $^3$-[H]-thymidine incorporation, as described by Reinhold et al. (Reinhold D. et al.: Inhibitors of dipeptidyl peptidase IV induce secretion of transforming growth factor β1 in PWM-stimulated PBMNC and T cells; Immunology 1997, 91: 354-360). FIG. 2 (page 2/14) shows the dose-dependent, more than additive to superadditive inhibition of the DNA synthesis.

EXAMPLE 3

Figure 3:
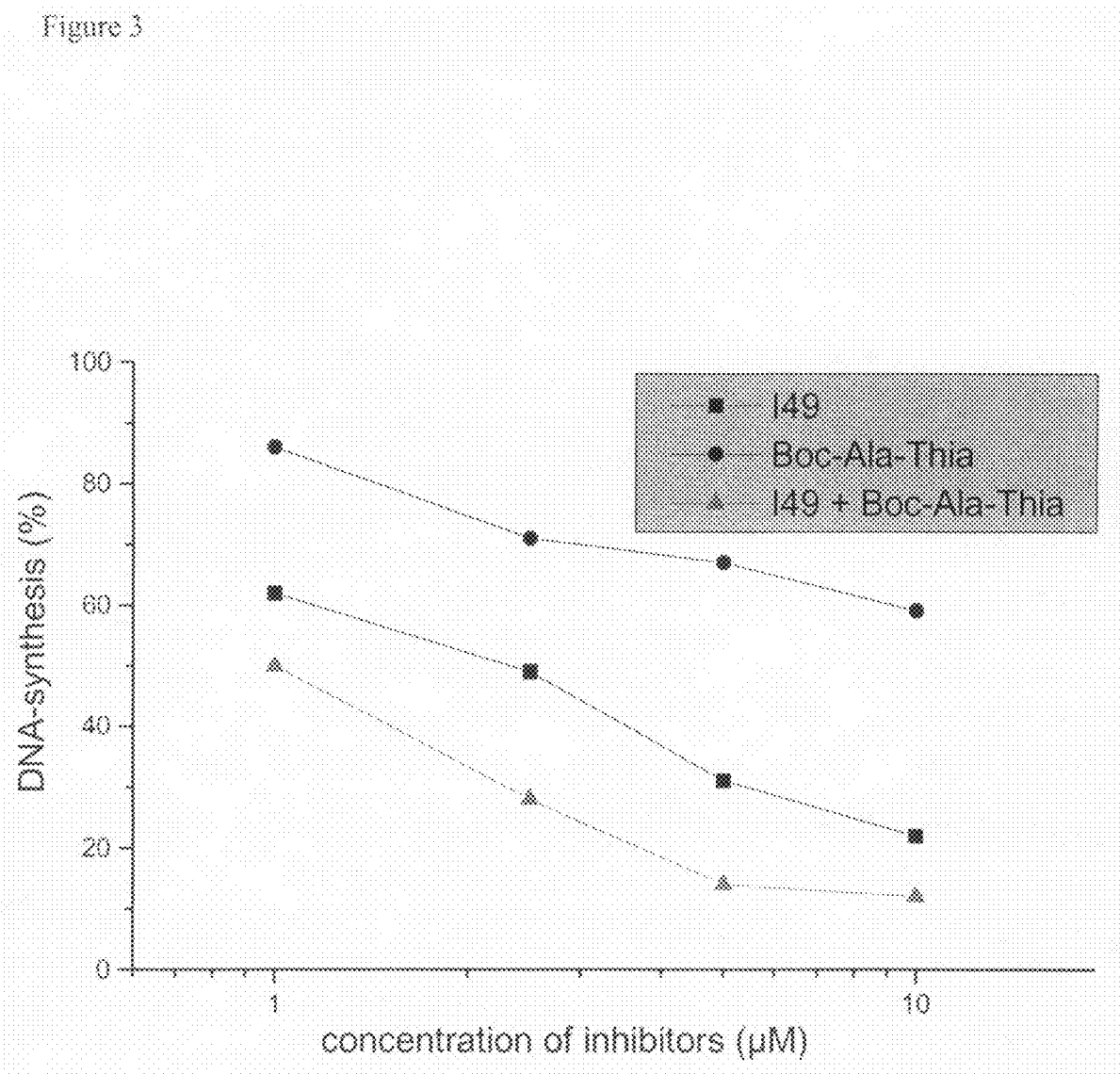
FIG. 3: Synergistic and dose-dependent effect of inhibitors of DP IV (149) and of prolyl oligopeptidase (Boc-Ala-Thia) on the DNA synthesis of human peripheral T lymphocytes. Human T cells were incubated for three days with the above-indicated concentrations of the inhibitors. Subsequently, $^3$-[H]-methyl thymidine was added to the culture medium, and after further 6 hours, the $^3$-[H]-thymidine amount incorporated into the DNA was measured.

Inhibition of the DNA Synthesis of Human T Lymphocytes by an Incubation with Synthetic Inhibitors of DP IV and of POP The searches according to the invention show that the DNA synthesis of human T lymphocytes is inhibited, in a more than additive to superadditive manner, by a simultaneous administration of inhibitors of DP TV (Lys[Z(NO$_2$)]-thiazolidide=I49) and of prolyl oligopeptidase (Boc-Ala thiazolidide). The T cells were incubated for 72 h in the presence of said inhibitors, and the DNA synthesis was determined subsequently by a measurement of the $^3$-[H]-thymidine incorporation, as described by Reinhold et al. (Reinhold D. et al.: Inhibitors of dipeptidyl peptidase IV induce secretion of transforming growth factor 131 in PWM-stimulated PBMNC and T cells; Immunology 1997, 91: 354-360). FIG. 3 (page 3/14) shows the dose-dependent, more than additive to superadditive inhibition of the DNA synthesis.

EXAMPLE 4

Figure 4:
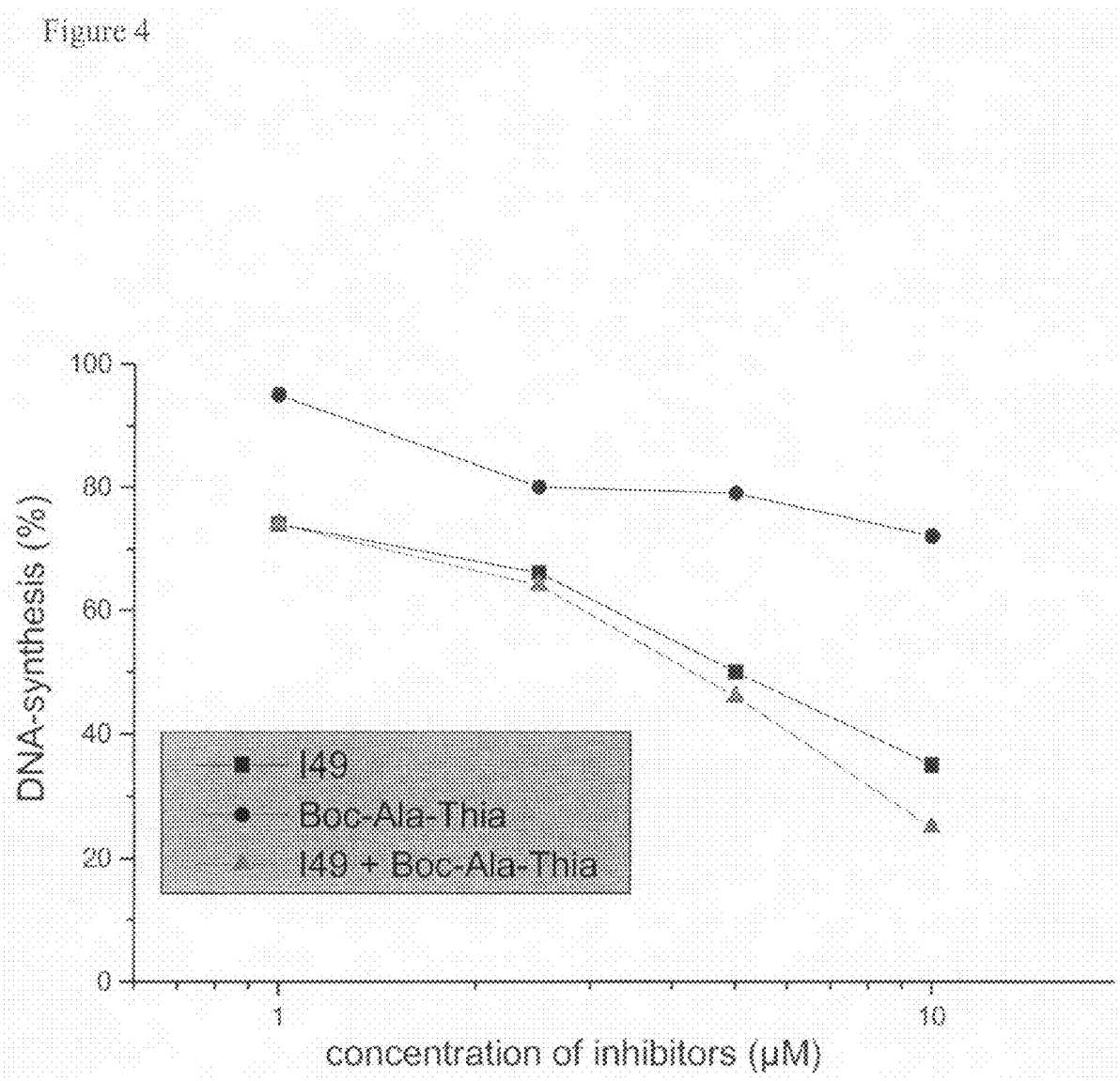
FIG. 4: Enhanced and dose-dependent effect of inhibitors of DP IV (149) and of prolyl oligopeptidase (Boc-Ala-Thia) on the DNA synthesis of human mononuclear cells (MNC). Human MNC were incubated for three days with the above-indicated concentrations of the inhibitors. Subsequently, $^3$-[H]-methyl thymidine was added to the culture medium, and after further 6 hours, the $^3$-[H]-thymidine amount incorporated into the DNA was measured.

Inhibition of the DNA Synthesis of Human Peripheric Mononuclear Cells by an Incubation with Synthetic Inhibitors of DP IV and of POP The searches according to the invention show that the DNA synthesis of human peripheric mononuclear cells (MMC) is inhibited, in an increased manner, by a simultaneous administration of inhibitors of DP IV (Lys[Z(NO$_2$)]-thiazolidide=I49) and of prolyl oligopeptidase (Boc-Ala thiazolidide). The MNC were incubated for 72 h in the presence of said inhibitors, and the DNA synthesis was determined subsequently by a measurement of the $^3$-[H]-thymidine incorporation, as described by Reinhold et al. (Reinhold D. et al.: Inhibitors of dipeptidyl peptidase IV induce secretion of transforming growth factor 131 in PWM-stimulated PBMNC and T cells; Immunology 1997, 91: 354-360). FIG. 4 (page 4/14) shows the dose-dependent, increased inhibition of the DNA synthesis.

EXAMPLE 5

Figure 5:
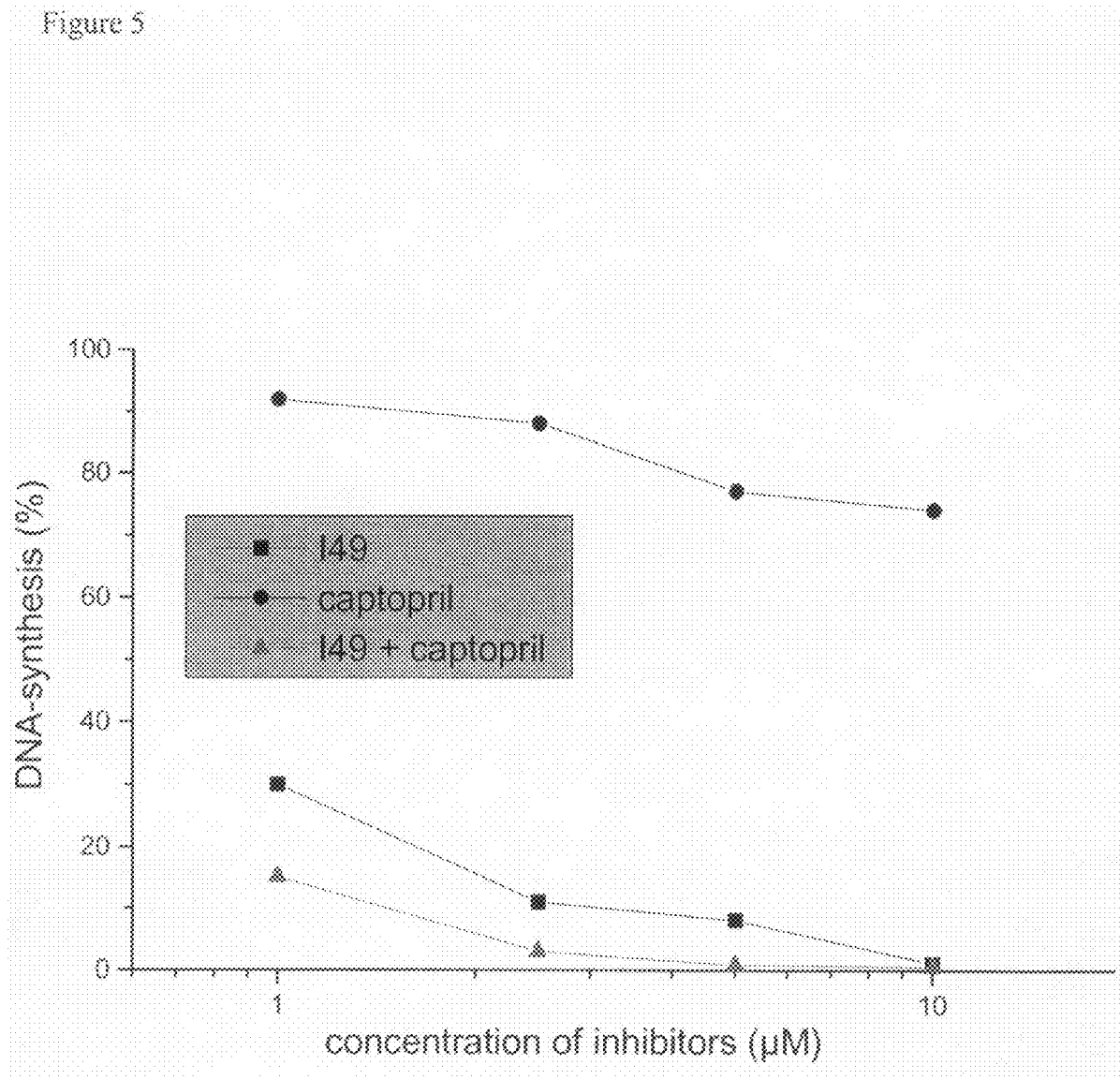
FIG. 5: Synergistic and dose-dependent effect of inhibitors of DP IV (149) and of angiotensin-converting enzyme (captopril) on the DNA synthesis of human peripheric T lymphocytes. Human T cells were incubated for three days with the above-indicated concentrations of the inhibitors. Subsequently, $^3$-[H]-methyl thymidine was added to the culture medium, and after further 6 hours, the $^3$-[H]-thymidine amount incorporated into the DNA was measured.

Inhibition of the DNA Synthesis of Human T Lymphocytes by an Incubation with Synthetic Inhibitors of DP IV and of ACE The searches according to the invention show that the DNA synthesis of human T lymphocytes is inhibited, in a more than additive to superadditive manner, by a simultaneous administration of inhibitors of DP IV (Lys[Z(NO$_2$)]-thiazolidide=I49) and of the angiotens-inconverting enzyme (Captopril). The T cells were incubated for 72 h in the presence of said inhibitors, and the DNA synthesis was determined subsequently by a measurement of the $^3$-[H]-thymidine incorporation, as described by Reinhold et al. (Reinhold D. et al.: Inhibitors of dipeptidyl peptidase IV induce secretion of transforming growth factor 131 in PWM-stimulated PBMNC and T cells; Immunology 1997, 91: 354-360). FIG. 5 (page 5/14) shows the dose-dependent, more than additive to superadditive inhibition of the DNA synthesis.

EXAMPLE 6

Figure 6:
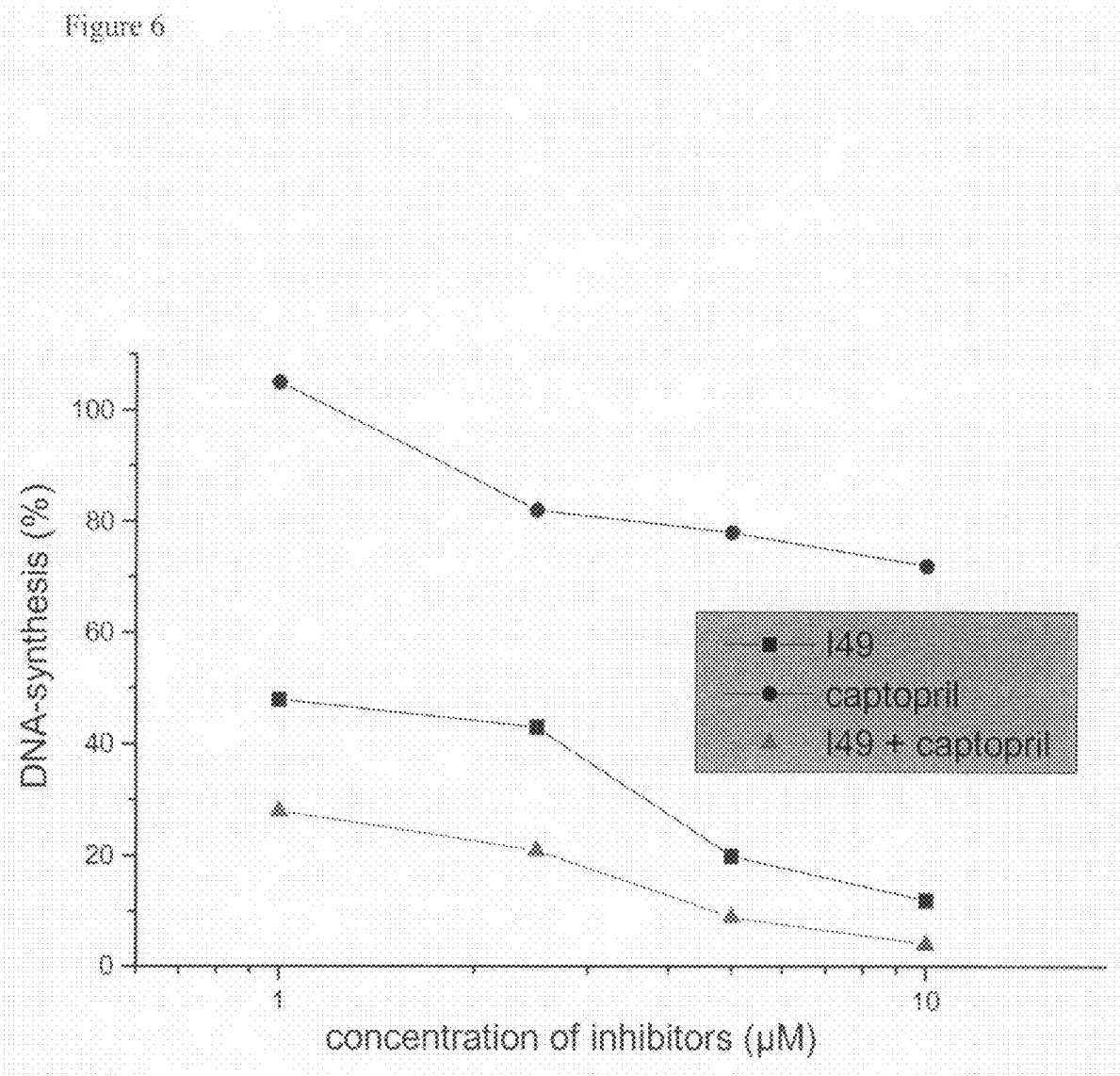
FIG. 6: Synergistic and dose-dependent effect of inhibitors of DP IV (149) and of angiotens-inconverting enzyme (captopril) on the DNA synthesis of human mononuclear cells (MNC). Human MNC were incubated for three days with the above-indicated concentrations of the inhibitors. Subsequently, $^3$-[H]-methyl thymidine was added to the culture medium, and after further 6 hours, the $^3$-[H]-thymidine amount incorporated into the DNA was measured.

Inhibition of the DNA Synthesis of Human Peripheric Mononuclear Cells by an Incubation with Synthetic Inhibitors of DP IV and of ACE The searches according to the invention show that the DNA synthesis of human peripheric mononuclear cells (MNC) is inhibited, in a more than additive to superadditive manner, by a simultaneous administration of inhibitors of DP IV (Lys[Z(NO$_2$)]-thiazolidide=I49) and of the angiotensin-converting enzyme (Captopril). The MNC were incubated for 72 h in the presence of said inhibitors, and the DNA synthesis was determined subsequently by a measurement of the $^3$-[H]-thymidine incorporation, as described by Reinhold et al. (Reinhold D. et al.: Inhibitors of dipeptidyl peptidase IV induce secretion of transforming growth factor 131 in PWM-stimulated PBMNC and T cells; Immunology 1997, 91: 354-360). FIG. 6 (page 6/14) shows the dose-dependent, more than additive to superadditive inhibition of the DNA synthesis.

EXAMPLE 7

Figure 7:
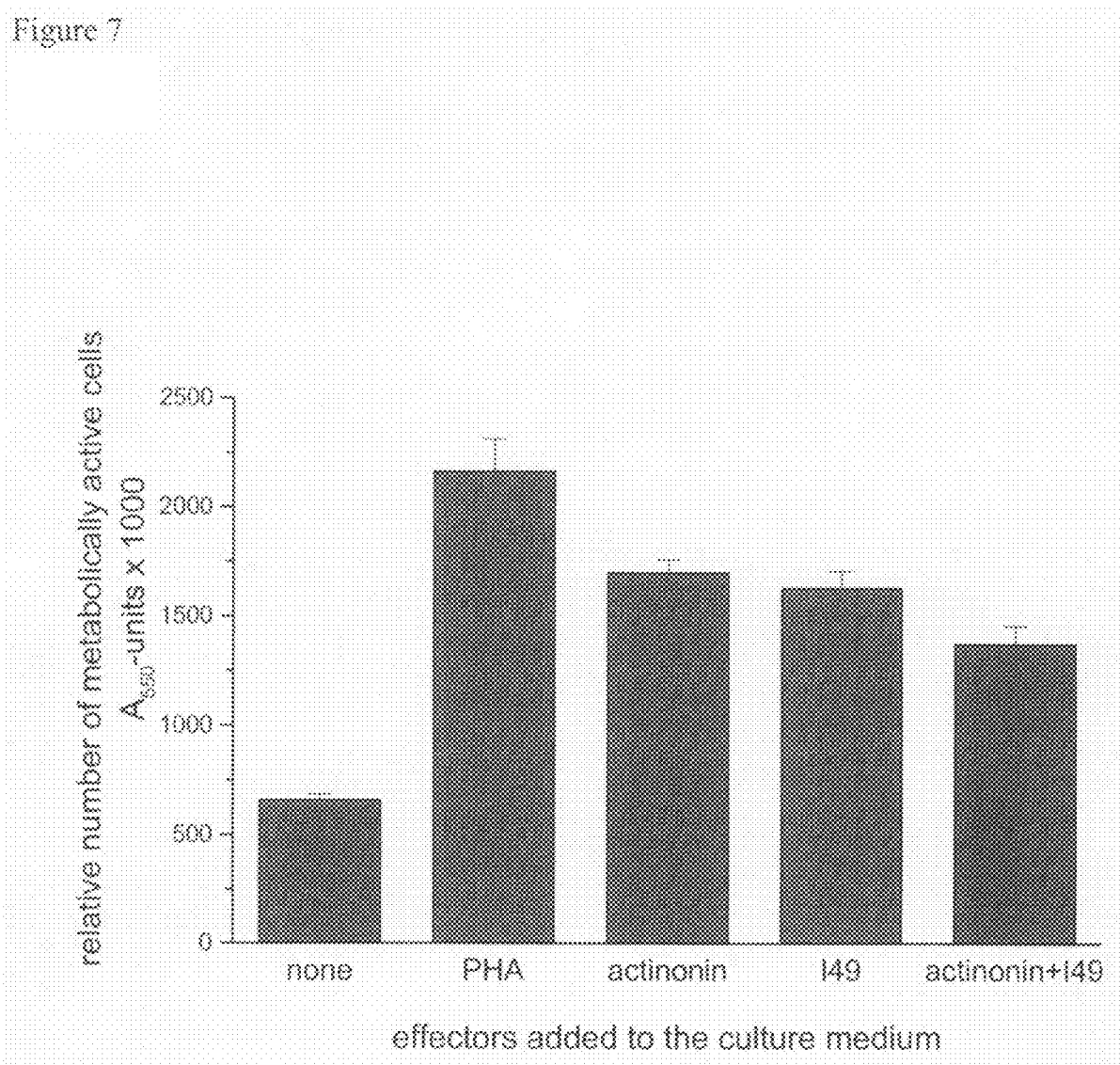
FIG. 7: The MNC were incubated for the time of 72 hours without (control), with mitogenic lectin phytohemagglutinine (PHA) or with PHA plus the inhibitors indicated. Subsequently, there was carried out a determination of the number of metabolically active cells by using the commercially available WST-1 Cell-Proliferation Assay (Takara Inc.) in accordance with the proposals of the manufacturer.

Inhibition of the proliferation of human peripheric mononuclear cells (MNC) by a single and simultaneous administration of inhibitors of DP IV (149=Lys[Z(NO$_2$)]-thiazolidide) and APN (Actinonin). (FIG. 7: page 7/14)

EXAMPLE 8

Figure 8:
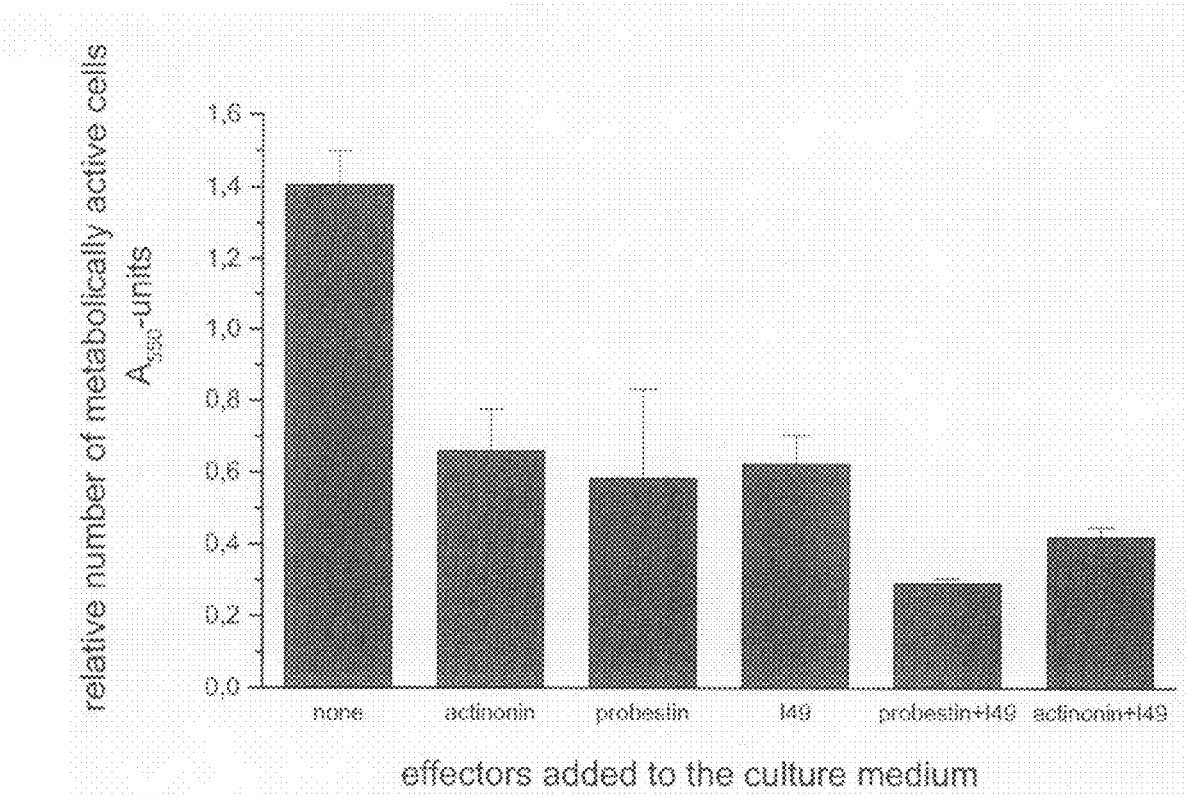
FIG. 8: The KARPAS-299-cells were incubated for a time period of 72 hours without (control) and with the above-indicated inhibitors singly or in combination. Subsequently, there was carried out a determination of the number of metabolically active cells by using the commercially available WST-1 Cell-Proliferation Assay (Takara Inc.) in accordance with the proposals of the manufacturer.

Inhibition of the proliferation of the human T cell line KARPAS-299 by a single and a simultaneous administration of inhibitors of DP IV (149=Lys[Z(NO$_2$)]-thiazolidide) and APN (Actinonin and Probestine). (FIG. 8: page 8/14)

EXAMPLE 9

Figure 9:
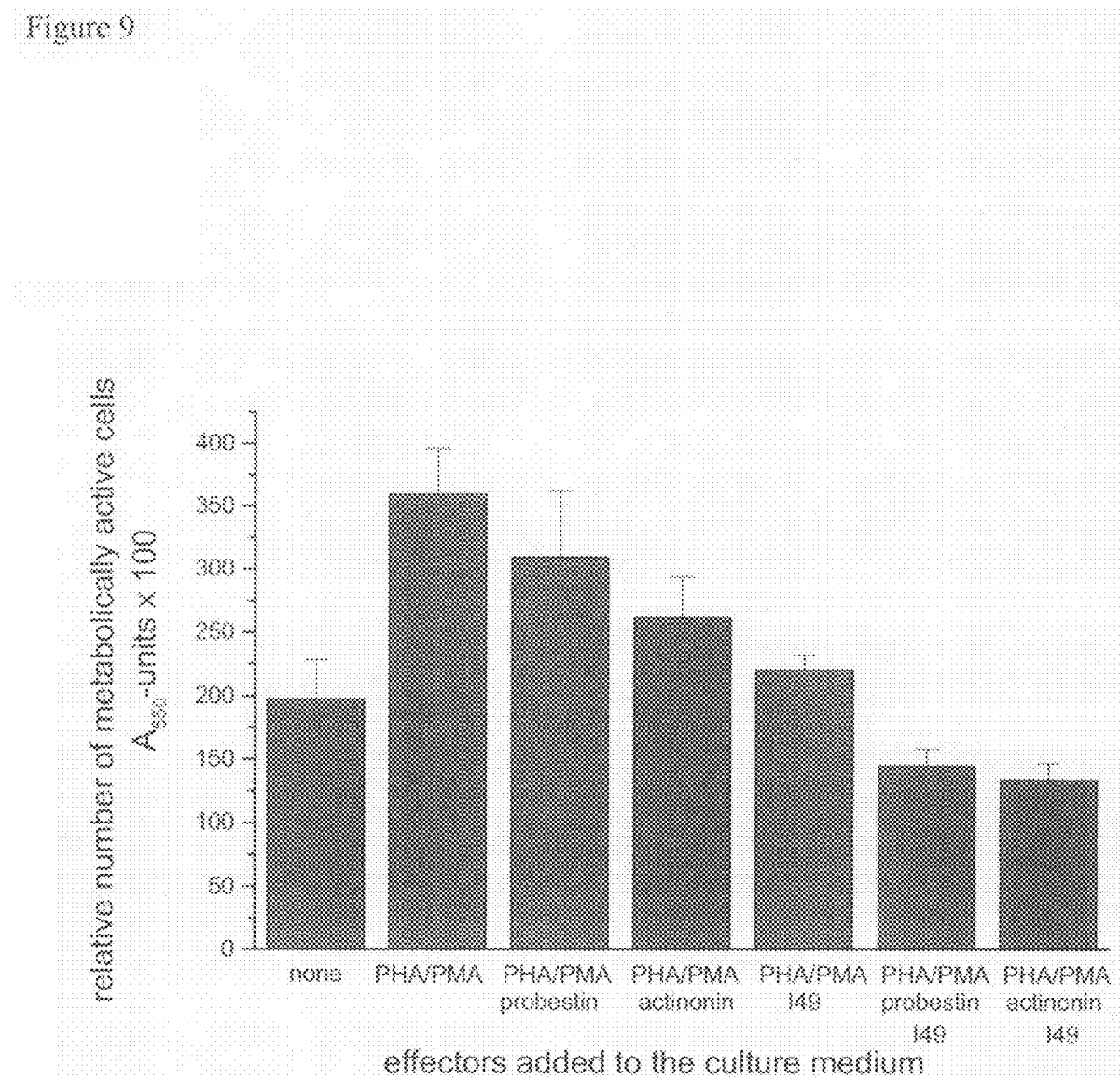
FIG. 9: The T cells with the exception of the untreated control, were activated by an addition of phytohemagglutinine and phorbol-12-myristate-13-acetate to the culture medium and were incubated for a time of 72 hours in the presence of the above inhibitors singly or in combination. Subsequently, there was carried out a determination of the number of metabolically active cells by using the commercially available WST-1 Cell-Proliferation Assay (Takara Inc.) in accordance with the proposals of the manufacturer.

Inhibition of the proliferation of activated human peripheric T cells by a single and simultaneous administration of inhibitors of DP IV (149=Lys[Z(NO$_2$)]-thiazolidide) and of APN (Actinonin and Probestine). (FIG. 9: page 9/14)

EXAMPLE 10

Figure 10:
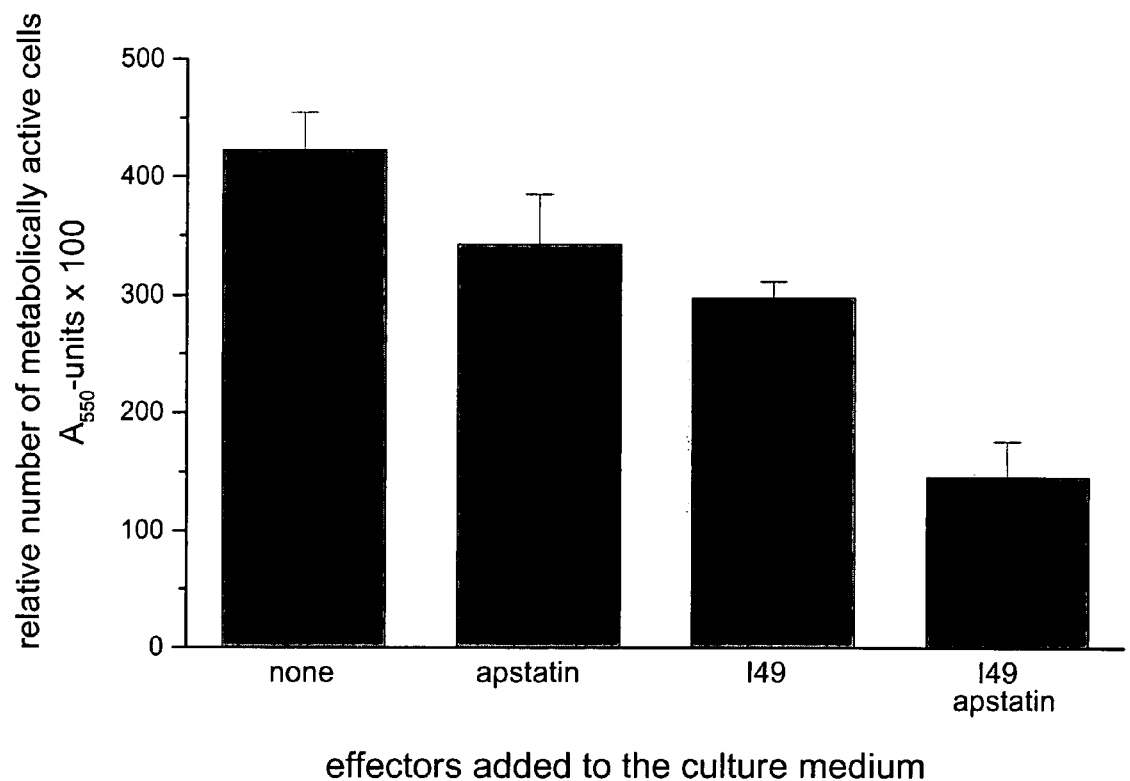
FIG. 10: The mononuclear cells (MNC) were incubated for a time of 72 hours in the presence of the above-indicated inhibitors singly or in combination. Subsequently, there was carried out a determination of the number of metabolically active cells by using the commercially available WST-1 Cell-Proliferation Assay (Takara Inc.) in accordance with the proposals of the manufacturer.

Inhibition of the proliferation of PHA-activated human nuclear cells (MNC) by a single and simultaneous administration of inhibitors of DP IV (149=Lys[Z(NO$_2$)]-thiazolidide) and of X-Pro-Aminopeptidase (APP) (Apstatine). (FIG. 10: page 10/14)

EXAMPLE 11

Inhibition of the DNA synthesis of pokeweed-mitogen (PWM) stimulated human mononuclear cells (MNC) of the peripheral blood by an incubation with synthetic inhibitors of DP IV and APN.

Figure 11:
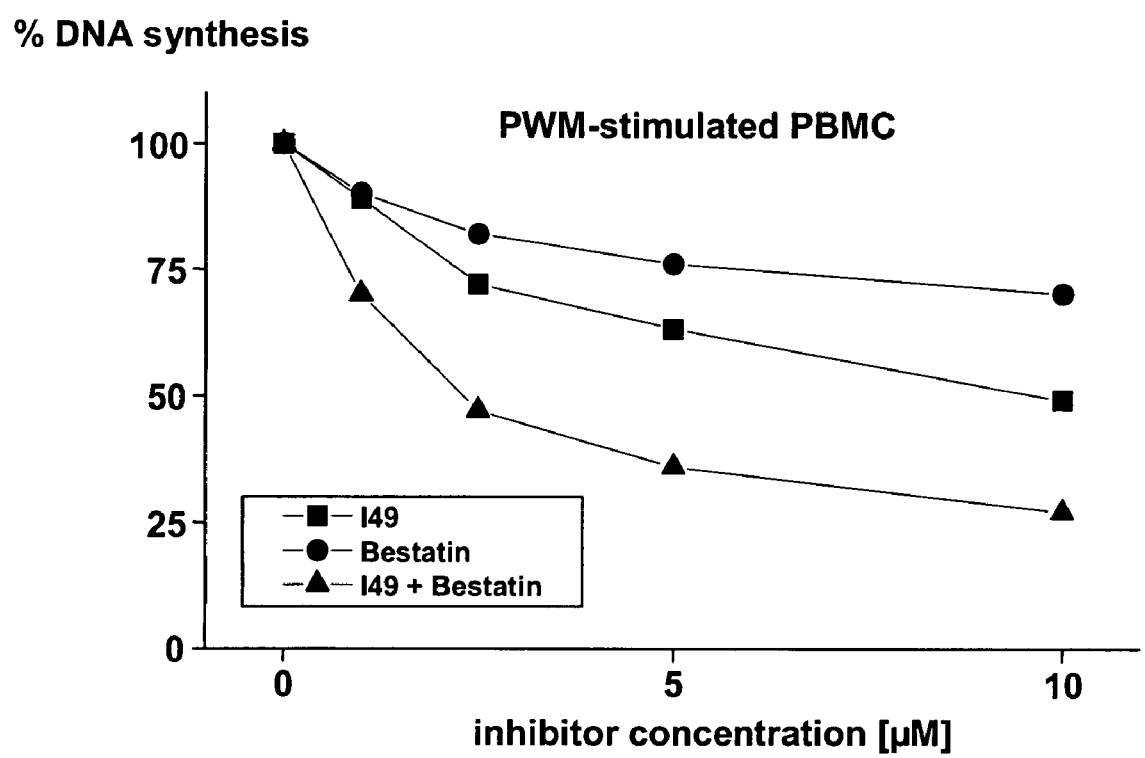
FIG. 11: Synergistic and dose-dependent effect of inhibitors of DP IV (149) and of aminopeptidase N (bestatine) on the DNA synthesis of human PWM-stimulated MNC. Human peripheral MNC were incubated for three days with PWM (2 µg/ml) and the above-indicated concentration of inhibitors. Subsequently, $^3$-[H]-methyl thymidine was added to the culture medium, and the amount of $^3$-[H]-thymidine incorporated into the DNA was measured after further 6 hours.

The searches according to the invention show that the DNA synthesis of pokeweed-mitogen stimulated human MNC of the peripheral blood is inhibited, in a more than additive manner, by a simultaneous administration of inhibitors of DP IV (Lys[Z(NO$_2$)]-thiazolidide=I49) and APN (Bestatine). The MNC were incubated for 72 hours in the presence of pokeweed-mitogen and of said inhibitors, and the DNA synthesis was determined subsequently by a measurement of the $^3$-[H]-thymidine-incorporation, is described by Reinhold et al. (Reinhold D et al.: Inhibitors of dipeptidyl peptidase IV induce secretion of transforming growth factor 131 in PWM-stimulated PBMNC and T cells. Immunology 1997; 91; 354-360). FIG. 11 (page 11/14) shows the dose-dependent more than additive inhibition of DNA synthesis.

EXAMPLE 12

Figure 12:
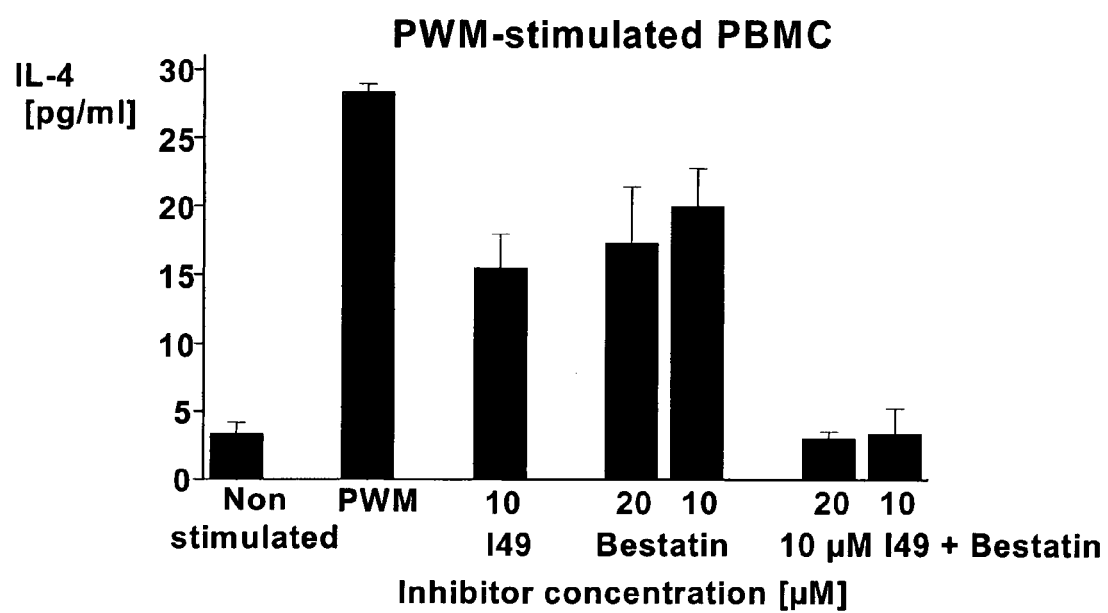
FIG. 12: Synergistic and dose-dependent effect of inhibitors of DP IV (149) and of aminopeptidase N (bestatine) on the IL-4-production by human, PWM-stimulated MNC. Human peripheral MNC were incubated for 48 hours with PWM (2 µg/ml) and with the above-indicated concentrations of the inhibitors. Subsequently, the concentration of IL-4 in the respective culture supernatants were measured by means of IL-4-ELISA.

Inhibition of the IL-4-production by pokeweed-mitogen stimulated human mononuclear cells of the peripheral blood by an incubation with synthetic inhibitors of DP IV and of APN The searches according to the invention show the interesting result that the production of the (TH2-cell characteristic) cytokine IL-4 by pokeweed-mitogen stimulated human mononuclear cells (MNC) of the peripheral blood is inhibited, in a more than additive to superadditive manner, by a simultaneous administration of inhibitors of DP IV (Lys[Z(NO$_2$)]-thiazolidide=I49) and APN (Bestatine). The MNC were incubated for 48 hours in the presence of pokeweed-mitogen and of said inhibitors, and the concentration of IL-4 was subsequently determined in the respective culture supernatants by means of commercially available IL-4 analysis kids (ELISA) as described by Reinhold et al. (Reinhold D et al.: Inhibitors of dipeptidyl peptidase IV induce secretion of transforming growth factor β1 in PWM-stimulated PBMNC and T cells. Immunology 1997; 91; 354-360). FIG. 12 (page 12/14) shows the dose-dependant superadditive inhibition of the IL-4-production.

EXAMPLE 13

Inhibition of the DNA synthesis of human keratinocytes (HaCaT cell line) by an incubation with synthetic inhibitors of DP IV and of APN.

The searches according to the invention show that the DNA synthesis of human HaCaT keratinocytes is inhibited, in a more than additive and, at lower concentrations, also in a superadditive manner, by a simultaneous administration of inhibitors of DP IV (Lys[Z(NO$_2$)]-thiazolidide=I49) and of APN (actinonin).

Figure 13:
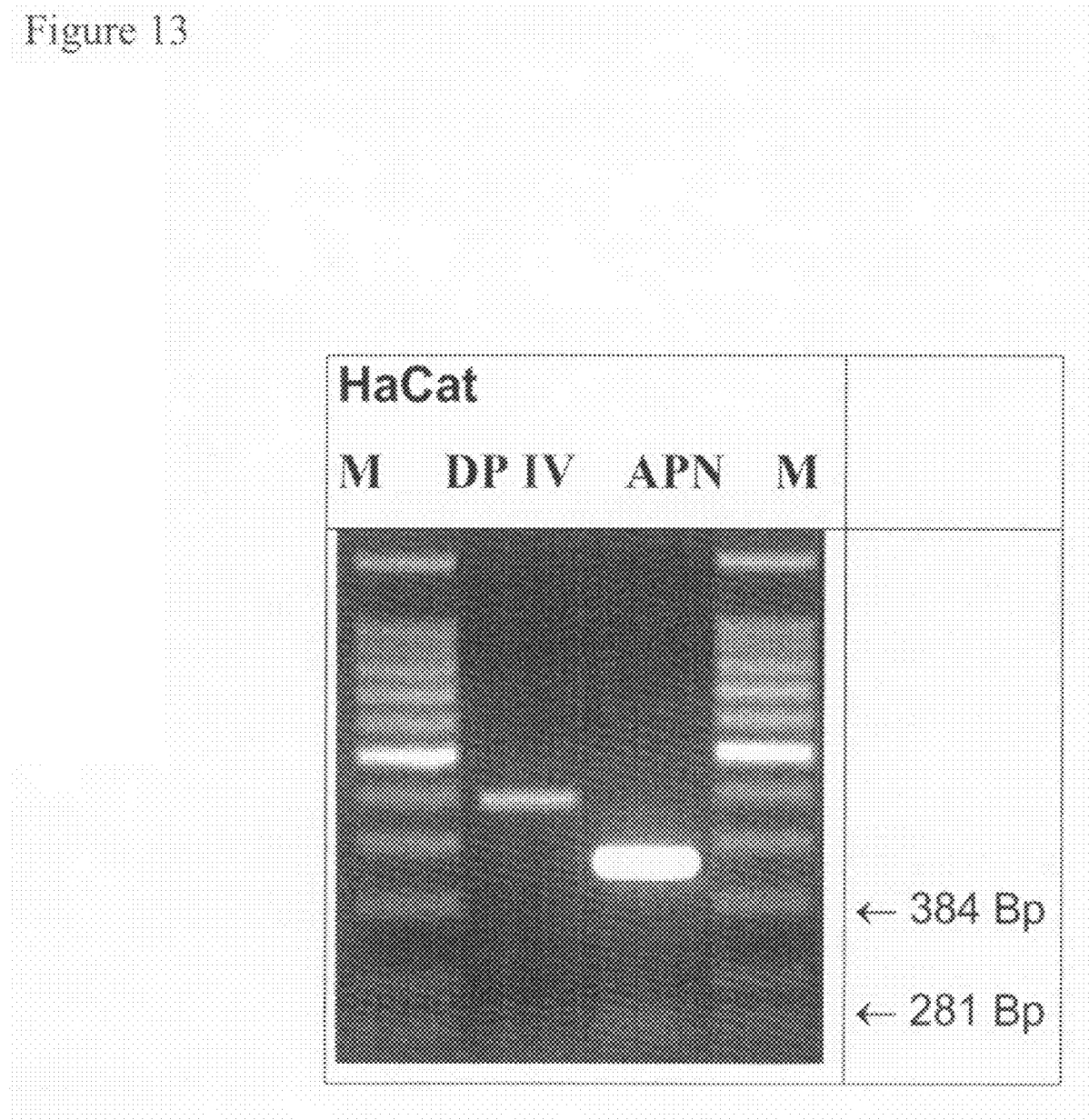
FIG. 13: Detection of the mRNA expression of DP IV and APN on HaCaT keratinocytes by means of RT-PCR.

The human keratinocyte cell line HaCaT which is an accepted cell model for psoriasis expresses DP IV and APN. The enzymatic activity of DP IV in vital cells is 30.2±5 pkat/10$^6$ cells, and the enzymatic activity of APN is 90±4 pkat/10$^6$ cells. In a corresponding manner, the mRNA of APN and DP IV is detectable on those cells (FIG. 13, page 13/14).

Figure 14:
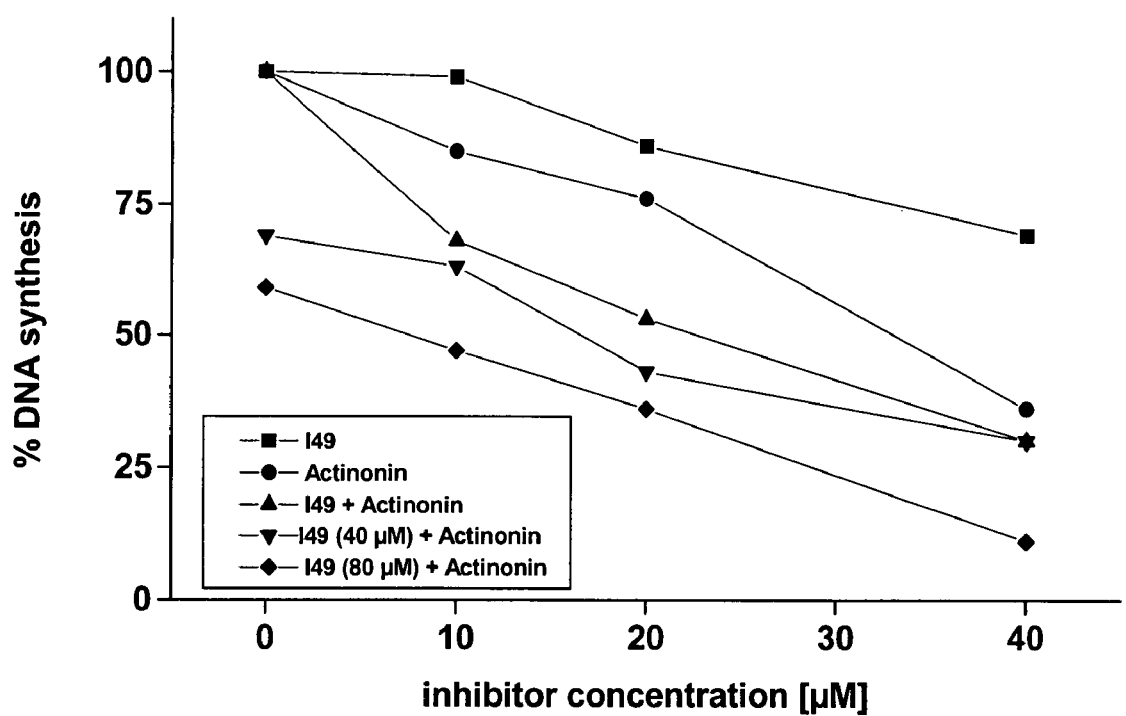
FIG. 14: Synergistic and dose-dependant effect of inhibitors of DP IV (149) and of aminopeptidase N (actinonin) on the DNA synthesis of human HaCaT keratinocytes. The cells were incubated for 48 hours with the above-indicated concentrations of inhibitors. Subsequently, $^3$-[H]-methyl thymidine was added to the culture medium, and after further 6 hours, the amount of $^3$-[H]-thymidine incorporated into the DNA was measured.

HaCaT cells were incubated for 48 hours in presence of the above-mentioned inhibitors, and the DNA synthesis was subsequently determined by a measurement of $^3$-[H]-thymidine-incorporation, as described by Reinhold et al. (Reinhold D et al.: Inhibitors of dipeptidyl peptidase IV induce secretion of transforming growth factor 131 in PWM-stimulated PBMNC and T cells. Immunology 1997; 91; 354-360). FIG. 14 (page 14/14) shows the dose-dependant inhibition of the DNA synthesis.

We claim:

1. A method for producing in an individual in need of treatment for allergic reactions of type I a more than additive to superadditive inhibition of the activation, proliferation, and DNA-synthesis and production of T$_{H2}$ cytokines by, human T lymphocytes and mononuclear cells, comprising administering to the individual an effective amount of a composition comprising an inhibitor of dipeptidyl peptidase IV (DP IV) as well as of enzymes having the same substrate specificity (DP IV-analogous enzymatic activity) in combination with an inhibitor of alanyl-aminopeptidase (aminopeptidase N, APN) as well as of enzymes having the same substrate specificity (APN-analogous enzymatic activity).

2. The method according to claim 1, wherein the inhibitor of DP IV is selected from the group consisting of:
   amino acid (Xaa)-Pro-dipeptides or salts thereof, wherein Xaa is an α-amino acid or side chain protected derivative; and
   Xaa-Xaa-(Trp)-Pro-(Xaa)$_n$ peptides or salts thereof, wherein Xaa is an α-amino acid and n is an integer from 0 to 10; and
   Xaa-amide or salts thereof, wherein Xaa is an α-amino acid or a side chain protected derivative and wherein cyclic amines serve as the amide structure;
   and combinations thereof.

3. The method according to claim 2, wherein the Xaa-Pro-dipeptide is selected from dipeptide phosphonic acid diaryl ester, or a dipeptide boronic acid and salts thereof.

4. The method according to claim 3, wherein the dipeptide boronic acid is Pro-Boro-Pro.

5. The method according to claim 2, wherein the amino acid of the amino acid (Xaa)-amide is selected from N$^\epsilon$-4-nitrobenzyloxycarbonyl-L-lysine, L-proline, L-tryptophan, L-isoleucine and L-valine.

6. The method according to claim 2, wherein the cyclic amine is selected from pyrrolidine, piperidine and thiazolidine.

7. The method according to claim 2, wherein the amino acid (Xaa)-amide is selected from the group consisting of N$^\epsilon$-4-nitrobenzyloxycarbonyl-L-lysine thiazolidide, N$^\epsilon$-4-nitrobenzyloxycarbonyl-L-lysine pyrrolidide, N$^\epsilon$-4-nitrobenzyloxycarbonyl-L-lysine piperidide, N$^\epsilon$-4-nitrobenzyloxycarbonyl-L-lysine 2-cyanothiazolidide, N$^\epsilon$-4-nitrobenzyloxycarbonyl-L-lysine 2-cyanopyrrolidide and N$^\epsilon$-4-nitrobenzyloxycarbonyl-L-lysine 2-cyano-piperidide.

8. The method according to claim 1, wherein the inhibitor of APN is selected from the group consisting of Actinonin, Leuhistin, Phebestin, Amastatin, Bestatin, Probestin, RB3014, β-aminothiols, α-aminophosphinic acids, α-aminophosphinic acid derivatives and salts thereof.

9. The method according to claim 8, wherein the α-aminophosphinic acid derivative is D-Phe-ψ[PO(OH)—CH$_2$]-Phe-Phe or salts thereof.

10. The method according to claim 1, wherein the administration results in therapy of asthma bronchial or hay fever.

11. The method according to claim 1, wherein the composition is administered by a route selected from oral, transdermal, intravenous, subcutaneous, intracutaneous, intramuscular, rectal, vaginal and sublingual.

12. The method according to claim 1, wherein the composition is administered topically as a cream, ointment, paste, gel, solution, spray, liposome, shaken mixture, hydro-colloid dressing and instillative application.

13. The method according to claim 1, wherein two or more inhibitors of DP IV as well as of an inhibitor of an enzyme having DP IV-analogous enzymatic activity and of alanyl-aminopeptidase (aminopeptidase N, APN) as well as of an inhibitor of an enzyme having APN-analogous enzymatic activity are administered simultaneously or sequentially in combination with a carrier, auxiliary and/or additive substances.

14. The method according to claim 13, wherein the inhibitor of DP IV is selected from the group consisting of:
   amino acid (Xaa)-Pro-dipeptides or salts thereof, wherein Xaa is an α-amino acid or side chain protected derivative; and
   Xaa-Xaa-(Trp)-Pro-(Xaa)$_n$ peptides or salts thereof, wherein Xaa is an α-amino acid and n is an integer from 0 to 10; and
   Xaa-amides or salts thereof, wherein Xaa is an α-amino acid or a side chain protected derivative and wherein cyclic amines serve as the amide structure;
   and combinations thereof.

15. The method according to claim 14, wherein the Xaa-Pro-dipeptide is selected from dipeptide phosphonic acid diaryl ester, or a dipeptide boronic acid and salts thereof.

16. The method according to claim 14, wherein the amino acid of the amino acid (Xaa)-amide is selected from N$^\epsilon$-4-nitrobenzyloxycarbonyl-L-lysine, L-proline, L-tryptophan, L-isoleucine and L-valine.

17. The method according to claim 13, wherein the inhibitor of APN is selected from the group consisting of Actinonin, Leuhistin, Phebestin, Amastatin, Bestatin, Probestin, RB3014, β-aminothiols, α-aminophosphinic acids, α-aminophosphinic acid derivatives and salts thereof.

18. The method according to claim 8, wherein the α-aminophosphinic acid derivative is D-Phe-ψ[PO(OH)—CH$_2$]-Phe-Phe or salts thereof.

19. The method according to claim 13, wherein the administration results in therapy of asthma bronchial or hay fever.

* * * * *